United States Patent
Wataya et al.

(10) Patent No.: US 10,441,137 B2
(45) Date of Patent: Oct. 15, 2019

(54) IMAGE PICKUP UNIT AND ENDOSCOPE

(71) Applicant: OLYMPUS CORPORATION, Tokyo (JP)

(72) Inventors: Yuichi Wataya, Akiruno (JP); Akira Muramatsu, Musashino (JP); Yuki Nakayama, Mitaka (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/634,109

(22) Filed: Jun. 27, 2017

(65) Prior Publication Data

US 2017/0290497 A1 Oct. 12, 2017

Related U.S. Application Data

(63) Continuation of application No. PCT/JP2015/080369, filed on Oct. 28, 2015.

(30) Foreign Application Priority Data

Mar. 17, 2015 (JP) .................. 2015-053687

(51) Int. Cl.
*A61B 1/00* (2006.01)
*G02B 23/24* (2006.01)
(Continued)

(52) U.S. Cl.
CPC ...... *A61B 1/00096* (2013.01); *A61B 1/00188* (2013.01); *G02B 7/02* (2013.01); *G02B 23/243* (2013.01); *G02B 23/2423* (2013.01); *G02B 23/2438* (2013.01); *A61B 1/00* (2013.01); *A61B 1/05* (2013.01); *G02B 23/2476* (2013.01)

(58) Field of Classification Search
CPC .............. G02B 23/2423; G02B 23/243; G02B 23/2438; G02B 7/02; A61B 1/00096; A61B 1/00188
See application file for complete search history.

(56) References Cited

U.S. PATENT DOCUMENTS 6,251,068 B1 6/2001 Akiba et al.
2010/0063361 A1* 3/2010 Kuchimaru ........ A61B 1/00096
600/168

FOREIGN PATENT DOCUMENTS

EP  2 072 001 A2  6/2009
JP  10-127568 A  5/1998
(Continued)

OTHER PUBLICATIONS

International Search Report dated Feb. 2, 2016 issued in PCT/JP2015/080369.
(Continued)

*Primary Examiner* — Aaron B Fairchild
(74) *Attorney, Agent, or Firm* — Scully Scott Murphy & Presser, P.C.

(57) ABSTRACT

To provide an image pickup unit that can prevent axis deviation of a movable lens barrel and obtain high-quality picked-up image, a stopper member is positioned and fixed in a state in which the stopper member is abutted against an outer circumferential surface of a rear group lens barrel, movement of a movable lens barrel to a retraction side along a photographing optical axis is restricted by contact of a stopper section of the stopper member and an operation rod, and a movable lens is held in a position for realizing a second focal length.

10 Claims, 24 Drawing Sheets

(51) Int. Cl.
*G02B 7/02* (2006.01)
*A61B 1/05* (2006.01)

(56) References Cited

FOREIGN PATENT DOCUMENTS

| | | |
|---|---|---|
| JP | 2001-258823 A | 9/2001 |
| JP | 2002-209831 A | 7/2002 |
| JP | 2009-300761 A | 12/2009 |

OTHER PUBLICATIONS

Japanese Official Action dated Nov. 22, 2016 issued in JP2016-549408.
Extended Supplementary European Search Report dated Jul. 31, 2018in European Patent Application No. 15 88 5560.1.

* cited by examiner

IMAGE PICKUP UNIT AND ENDOSCOPE

CROSS REFERENCE TO RELATED APPLICATION

This application is a continuation application of PCT/JP2015/080369 filed on Oct. 28, 2015 and claims benefit of Japanese Application No. 2015-053687 filed in Japan on Mar. 17, 2015, the entire contents of which are incorporated herein by this reference.

BACKGROUND OF INVENTION

1. Field of the Invention

The present invention relates to an image pickup unit capable of changing an optical characteristic of an observation optical system and an endoscope in which the image pickup unit is provided.

2. Description of the Related Art

As is well known, endoscopes are widely used for observation, treatment, and the like in a body (in a body cavity) of an organism, inspection, repairing, and the like in a plant facility for industrial use, or the like. In recent years, among the endoscopes of this type, there has been an endoscope including an image pickup unit that can change a focal length by moving an observation optical system in a photographing optical axis direction for a zooming function for performing focus adjustment of a photographed image or magnification adjustment such as wide/tele. Note that a technique of the image pickup unit that can change the focal length in this way is used not only in the endoscope but also in various moving picture cameras.

In particular, in an endoscope requested to be reduced in size, an image pickup unit of a focus switching type focused when a movable lens unit (a movable lens barrel) provided in an observation optical system is present in a predetermined advanced position and a predetermined retracted position is widely adopted. In such an image pickup unit of the focus switching type, in order to realize an appropriate focused state even when there is machining tolerance of respective lenses and the like, in general, the advanced position of the movable lens barrel is adjusted by finely adjusting relative positions of respective fixed lens barrels and the like during assembly of the image pickup unit.

On the other hand, as a technique for adjusting the retracted position of the movable lens unit, for example, Japanese Patent Application Laid-Open Publication No. 2001-258823 discloses a technique for forming a screw section in an outer circumference of an abutting member of a pipe unit, with which the movable lens barrel is brought into contact in the retracted position, and finely adjusting a screwed state of the screw section with a lens cylinder unit (a fixed lens barrel) to thereby perform the adjustment of the retracted position of the movable lens barrel.

SUMMARY OF THE INVENTION

An image pickup unit according to an aspect of the present invention includes: an observation optical system of a focus switching type including a fixed lens and a movable lens; a fixed barrel that holds the fixed lens; a movable barrel disposed in the fixed barrel to be capable of advancing and retracting in a direction along a photographing optical axis of the observation optical system, the movable barrel holding the movable lens; and a stopper member positioned and fixed in a state in which the stopper member is abutted against an outer circumferential surface of the fixed barrel by surface contact, the stopper member restricting movement of the movable barrel in one direction of the photographing optical axis through contact with the movable barrel to thereby hold the movable lens in a position for realizing one focal length of the observation optical system.

An endoscope according to an aspect of the present invention includes the image pickup unit provided at a distal end portion of an insertion section inserted into a subject.

DETAILED DESCRIPTION OF THE PREFERRED EMBODIMENT(S)

Figure 1:
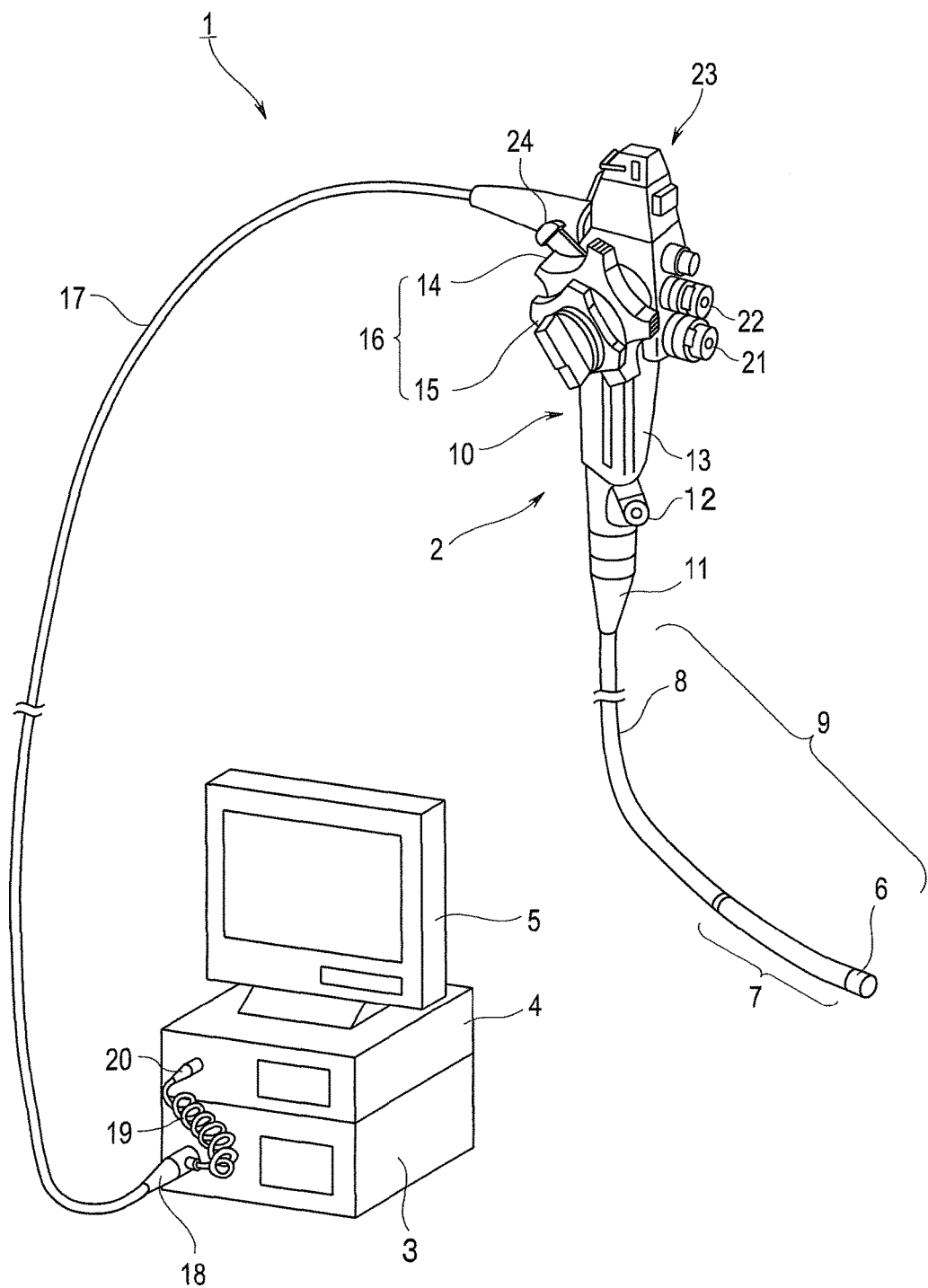
FIG. 1 is an explanatory diagram showing an overall configuration of an endoscope according to a first embodiment of the present invention.
Figure 2:
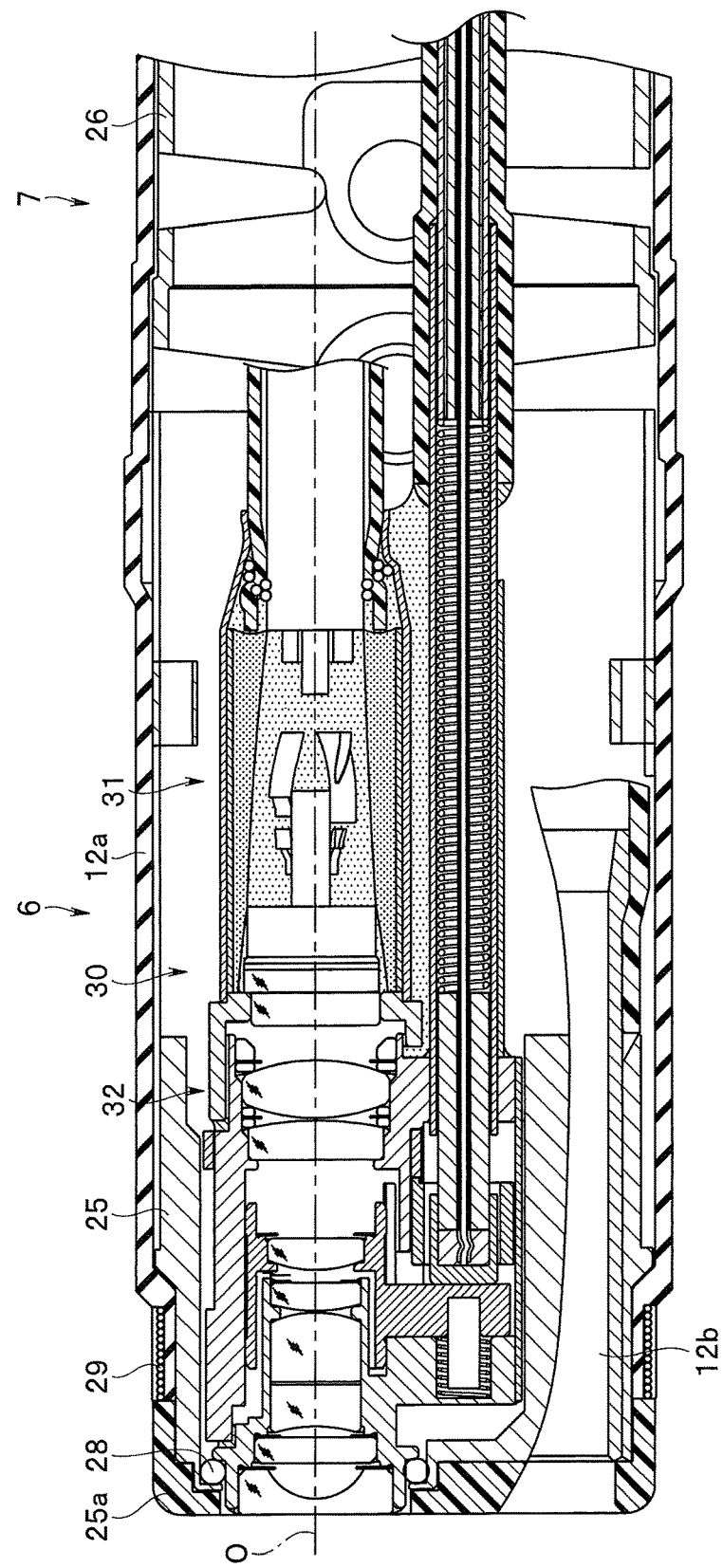
FIG. 2 is a sectional view showing an internal configuration of a distal end portion and a bending section according to the first embodiment of the present invention.
Figure 3:
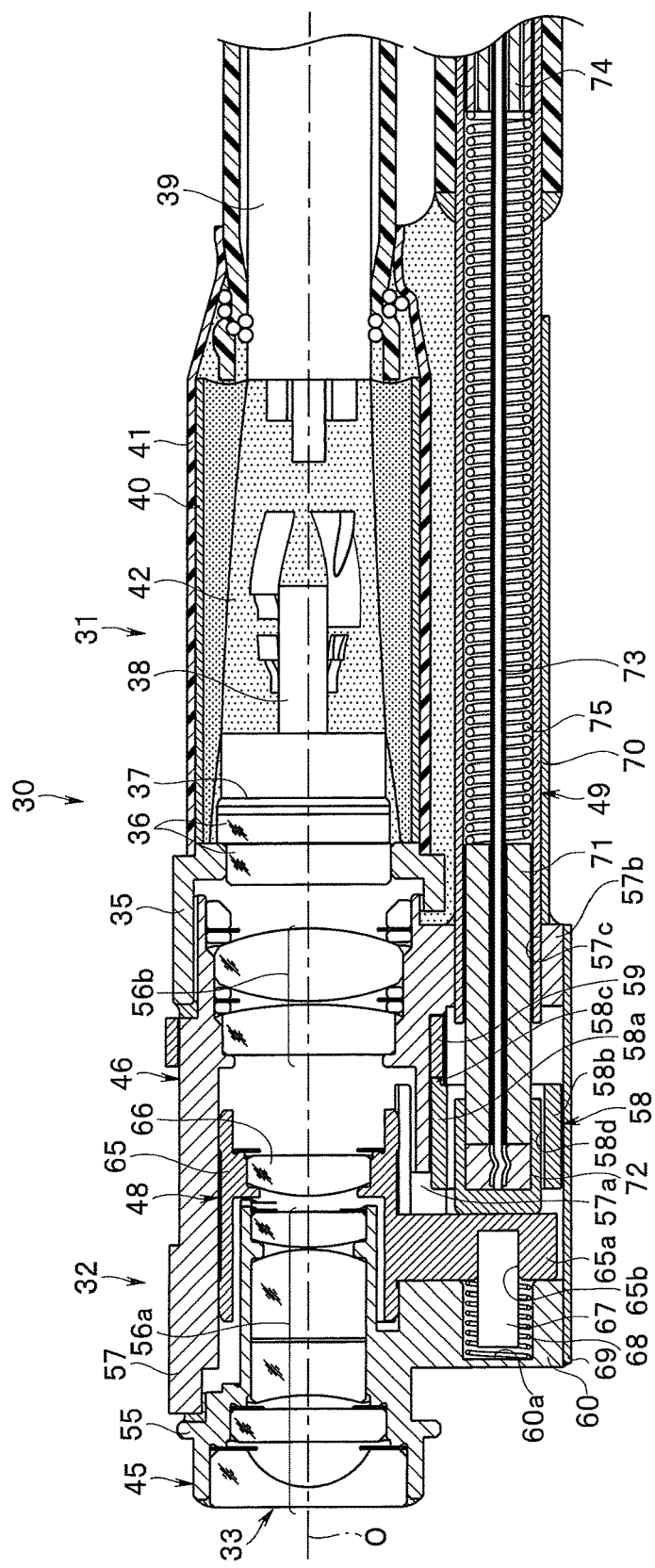
FIG. 3 is a sectional view showing a configuration of an image pickup unit in a state in which a movable lens unit moves to a forward advanced position according to the first embodiment of the present invention.
Figure 4:
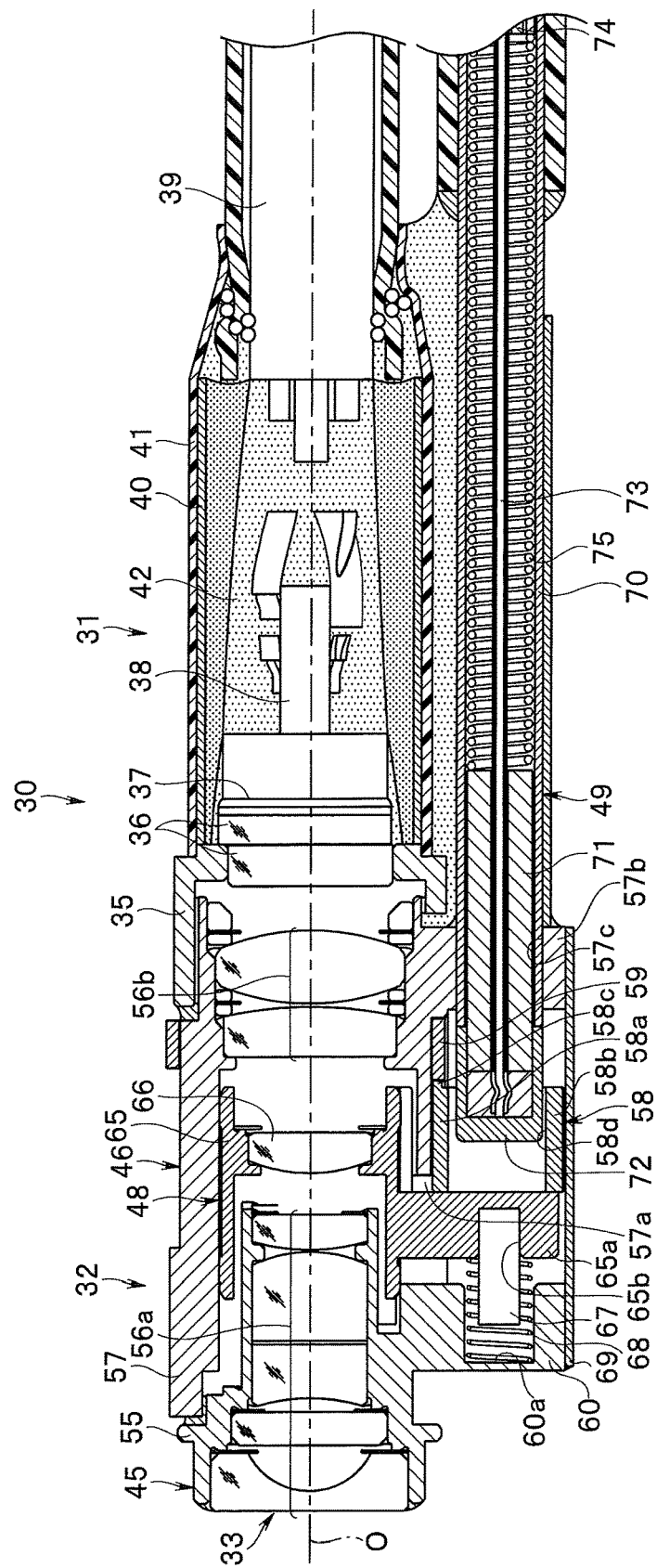
FIG. 4 is a sectional view showing the configuration of the image pickup unit in a state in which the movable lens unit moves to a rearward retracted position according to the first embodiment of the present invention.
Figure 5:
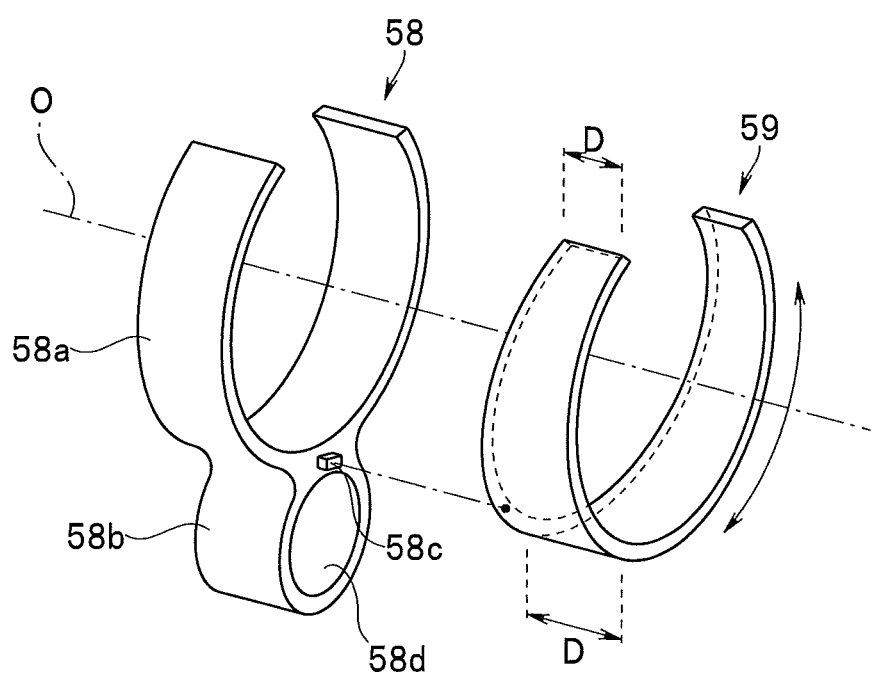
FIG. 5 is a perspective view showing a relation between a stopper member and an adjustment ring according to the first embodiment of the present invention.
Figure 6:
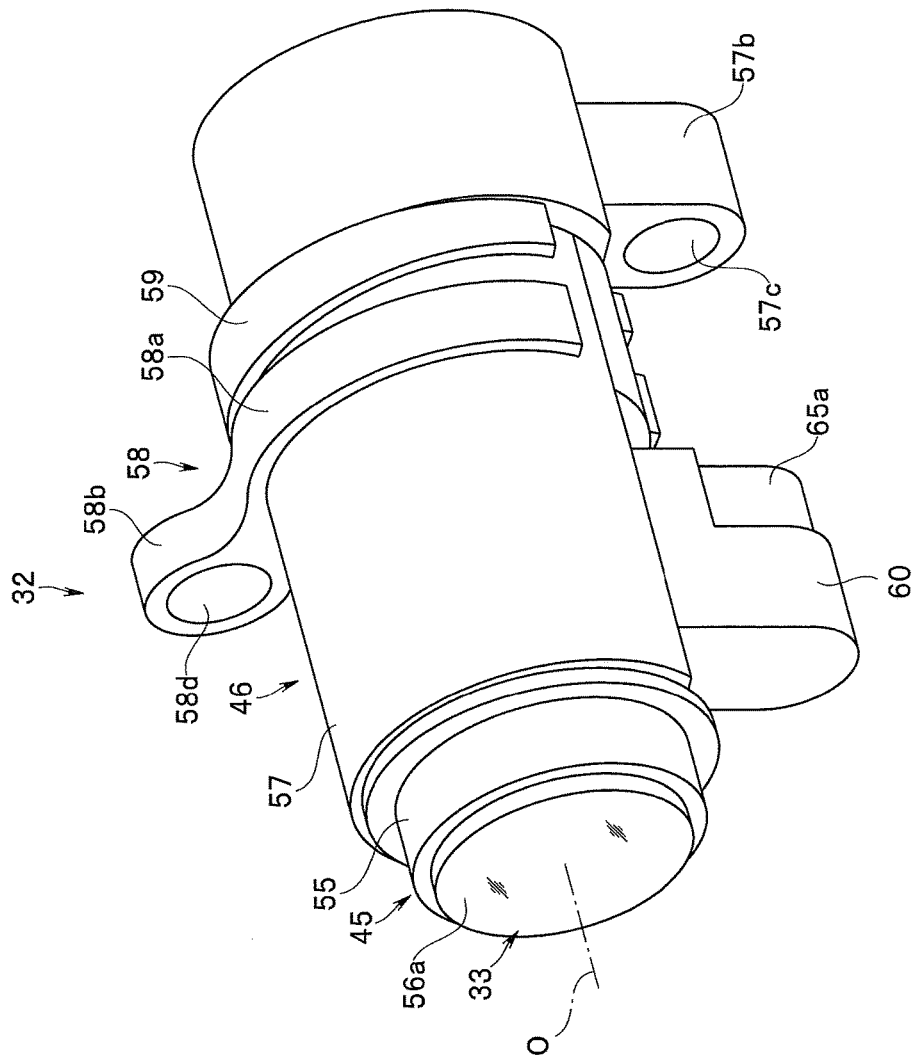
FIG. 6 is a perspective view showing an assembling process for the stopper member and the adjustment ring according to the first embodiment of the present invention.
Figure 7:
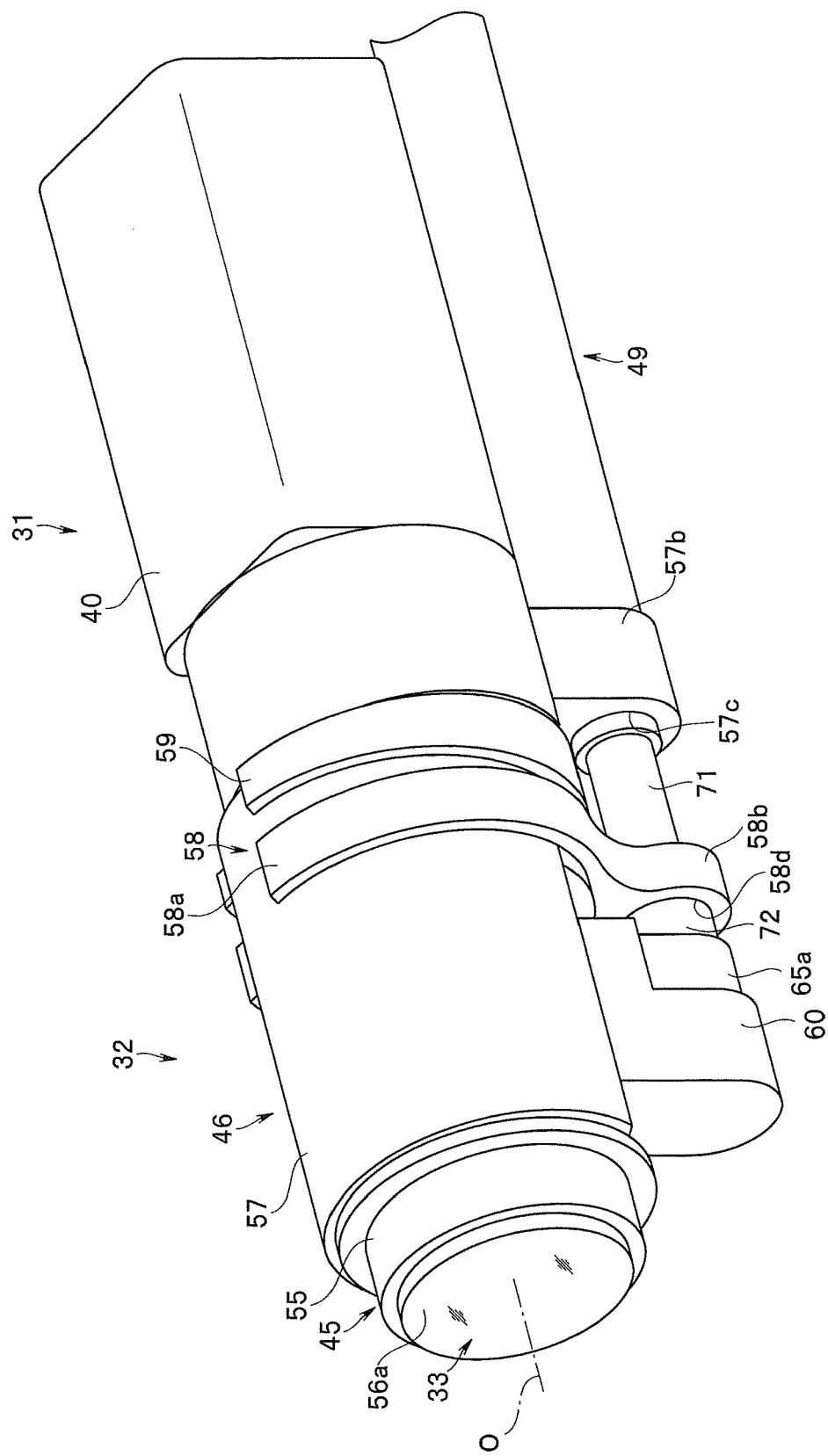
FIG. 7 is a perspective view of an image pickup unit according to the first embodiment of the present invention.

Modes of the present invention are explained below with reference to the drawings. The drawings relate to a first embodiment of the present invention. FIG. 1 is an explanatory diagram showing an overall configuration of an endoscope. FIG. 2 is a sectional view showing an internal configuration of a distal end portion and a bending section. FIG. 3 is a sectional view showing a configuration of an image pickup unit in a state in which a movable lens unit moves to a forward advanced position. FIG. 4 is a sectional view showing the configuration of the image pickup unit in a state in which the movable lens unit moves to a rearward retracted position. FIG. 5 is a perspective view showing a relation between a stopper member and an adjustment ring. FIG. 6 is a perspective view showing an assembling process for the stopper member and the adjustment ring. FIG. 7 is a perspective view of the image pickup unit.

As shown in FIG. 1, an electronic endoscope system (hereinafter simply referred to as endoscope system) 1 according to the present embodiment is configured by electrically connecting an electronic endoscope apparatus (hereinafter simply referred to as endoscope) 2 functioning as an endoscope, a light source apparatus 3, a video processor 4, and a color monitor 5.

The endoscope 2 includes an insertion section 9 and an operation section 10 from which the insertion section 9 is extended. A universal cord 17 extending from the operation section 10 is connected to the light source apparatus 3 via a scope connector 18.

A coil-shaped scope cable 19 is extended from the scope connector 18. An electric connector section 20 is provided on the other end side of the scope cable 19. The electric connector section 20 is connected to the video processor 4.

The insertion section 9 is configured by consecutively connecting a distal end portion 6, a bending section 7, and a flexible tube section 8 in order from a distal end side. A distal end opening section, an observation window, a plurality of illumination windows, an observation window cleaning port, and an observation object cleaning port, which are well known, (all of which are not shown in the figure) are disposed on a distal end face of the distal end portion 6.

On a rear surface side of the observation window, an image pickup unit explained below is disposed in the distal end portion 6. On a rear surface side of the plurality of illumination windows, a distal end side of a not-shown light guide bundle is disposed. The light guide bundle is inserted through and disposed on an inside of the universal cord 17 from the insertion section 9 through the operation section 10. When the scope connector 18 is connected to the light source apparatus 3, the light guide bundle is capable of transmitting illumination light of the light source apparatus 3 to the illumination windows.

The observation window cleaning port and the observation object cleaning port configure opening sections of not-shown two cleaning tubes inserted through the inside of the universal cord 17 from the distal end portion 6. The cleaning tubes are connected to a cleaning tank, in which cleaning water is stored, and a compressor (both of which are not shown in the figure) on the light source apparatus 3 side.

The operation section 10 includes a bend preventing section 11 from which the insertion section 9 is extended, a forceps port 12 disposed in a side section on a lower side, an operation section main body 13 configuring a grip section in a halfway section, a bending operation section 16 including two bending operation knobs 14, 15 provided on an upper side, an air/water-feeding control section 21, a suction control section 22, a switch section 23 configured from a plurality of switches and configured to mainly operate an image pickup function, and an operation lever 24 configured to advance and retract a movable lens provided in the image pickup unit explained below to operate, for example, a focusing function of focus adjustment or a zooming function for performing magnification adjustment such as wide/tele.

Note that a forceps port 12 of the operation section 10 configures an opening section of a not-shown treatment instrument channel mainly inserted through and disposed in the insertion section 9 to the distal end opening section of the distal end portion 6.

A configuration of the distal end portion 6 of the endoscope 2 is mainly explained with reference to FIG. 2.

As shown in FIG. 2, an image pickup unit 30 is disposed on an inside of the distal end portion 6. The image pickup unit 30 is fit and disposed in a rigid distal-end rigid member 25 and fixed to the distal-end rigid member 25 by a not-shown set screw from a side direction.

An O-shaped ring 28 for securing water tightness with the distal-end rigid member 25 is disposed in an outer circumferential section on a distal end side of the image pickup unit 30. A distal end cover 25a configuring the distal end face of the distal end portion 6 is bonded and fixed to a distal end side of the distal-end rigid member 25.

Note that the distal end opening section, which is a hole section, formed in the distal end cover 25a configures an opening section of a treatment instrument channel 12b in the distal end portion 6 as explained above.

A plurality of bending pieces 26 configuring the bending section 7 are consecutively connected on a proximal end side of the distal-end rigid member 25. Outer circumferences of the distal-end rigid member 25 and the bending pieces 26 are integrally covered by a distal-end-insertion-section rubber member 12a. A distal-end outer circumferential section of the distal-end-insertion-section rubber member 12a is fixed to the distal-end rigid member 25 by a bobbin adhesive section 29.

Note that members such as the cleaning tube and the light guide bundle for illumination disposed at the distal end portion 6 are conventionally well-known components. Therefore, explanation of the members is omitted.

A detailed configuration of the image pickup unit 30 is explained with reference to FIG. 3 to FIG. 7.

As shown in FIGS. 3, 4, and 7, the image pickup unit 30 in the present embodiment includes a solid-state image pickup device unit 31 and an observation optical system unit 32 consecutively connected to a distal end side of the solid-state image pickup device unit 31.

The solid-state image pickup device unit 31 includes a solid-state-image-pickup-device holding frame 35. A front surface side of a solid-state image pickup device chip 37 including a CCD, a CMOS, or the like is held in the solid-state-image-pickup-device holding frame 35 via an optical member 36 such as cover glass. A laminated substrate 38 is electrically connected to a rear surface side of the solid-state image pickup device chip 37 via a not-shown FPC or the like. A plurality of communication lines branching from a cable 39 are connected to the laminated substrate 38. The cable 39 is inserted through and disposed on an inside of the endoscope 2 and electrically connected to the video processor via the electric connector section 20.

A reinforcing frame 40 is consecutively connected to a proximal-end outer circumferential section of the solid-state-image-pickup-device holding frame 35. A heat shrinkage tube 41 covering up to a distal end portion of the cable 39 is provided in an outer circumference of the reinforcing frame 40. Note that, in a space formed by the reinforcing frame 40 and the heat shrinkage tube 41 from a proximal end portion of the solid-state-image-pickup-device holding frame 35, a protective agent 42 such as an adhesive for water-tightly retaining and protecting the solid-state image pickup device unit 31 is filled.

The observation optical system unit 32 in the present embodiment includes an observation optical system 33 of a focus switching type configured to advance and retract a lens on an inside and change an optical characteristic (a focal length) to thereby realize a focusing function or a zooming function.

More specifically, the observation optical system unit 32 includes a front group lens unit 45 located on a distal end side, a rear group lens unit 46 consecutively connected to a proximal end side of the front group lens unit 45, a movable lens unit 48 capable of advancing and retracting in a photographing optical axis O direction in the rear group lens unit 46, and an actuator 49 configured to cause the movable lens unit 48 to advance and retract.

The front group lens unit 45 includes a front group lens barrel 55, which is a fixed barrel, and a front group lens 56a including a plurality of fixed lenses held by the front group lens barrel 55.

The rear group lens unit 46 includes a rear group lens barrel 57, which is a fixed barrel, a distal end side of which externally fits in the front group lens barrel 55, and a rear group lens 56b including a plurality of fixed lenses held on the photographing optical axis O on a proximal end side of the rear group lens barrel 57.

The solid-state-image-pickup-device holding frame 35 is externally fit on the proximal end side of the rear group lens barrel 57. Consequently, the solid-state image pickup device unit 31 and the observation optical system unit 32 are coupled.

In the rear group lens barrel 57, a slit 57a piercing through an inner circumference side and an outer circumference side of the rear group lens barrel 57 is provided. The slit 57a is extended in a direction same as the photographing optical axis O direction. A distal end side of the slit 57a is opened at a distal end of the rear group lens barrel 57. In the rear group lens barrel 57, a holding rod 57b projecting in an outer diameter direction on a proximal end side of the slit 57a is provided. An actuator holding hole 57c piercing through in a coaxial direction with the photographing optical axis O is provided in the holding rod 57b.

In the rear group lens barrel 57, a stopper member 58 positioned and fixed in an abutted state against an outer circumferential surface of the rear group lens barrel 57 is provided. As shown in FIG. 5, the stopper member 58 in the present embodiment includes a ring section 58a having a C-shaped ring shape abutted against an outer circumferential surface of the rear group lens barrel 57 in a state of direct surface contact with the outer circumferential surface and a pipe-shaped stopper section 58b formed integrally with the ring section 58a. In a state in which the stopper section 58b is positioned to be opposed to the holding rod 57b in a predetermined position in the photographing optical axis O direction, the stopper member 58 is fixed by bonding the ring section 58a to the outer circumferential surface of the rear group lens barrel 57.

For example, in order to accurately perform positioning in the photographing optical axis O direction of the stopper member 58 on the basis of the holding rod 57b, an adjustment ring 59 is interposed between the holding rod 57b and the stopper member 58. The adjustment ring 59 is configured by a member having a C-shaped ring shape, width D in the photographing optical axis O direction of which linearly changes along a circumferential direction. The adjustment ring 59 is disposed such that one end of the adjustment ring 59 is in contact with the stopper member 58 and the other end is in contact with the holding rod 57b. The adjustment ring 59 is turned around the photographing optical axis O along the outer circumferential surface of the rear group lens barrel 57 to thereby change relative positions of the stopper member 58 and the holding rod 57b. As a result, the adjustment ring 59 adjusts a position in the photographing optical axis O direction of the stopper member 58 on the rear group lens barrel 57. That is, in the present embodiment, one end face of the adjustment ring 59 functions as a cam surface for changing the position in the photographing optical axis O direction of the stopper member 58. Consequently, the adjustment ring 59 realizes a function of an end-face-cam adjustment member capable of changing an abutting position against the stopper member 58 and adjusting the position in the photographing optical axis O direction of the stopper member 58 with respect to the rear group lens barrel 57, which is the fixed barrel.

In this case, in order to accurately move the stopper member 58 along the adjustment ring 59, it is desirable to provide, in the stopper member 58, a protrusion section 58c for coming into substantial point contact with the adjustment ring 59.

A front side stopper 60 opposed to the stopper section 58b is provided further on a distal end side than the rear group lens barrel 57. In the present embodiment, the front side stopper 60 is formed integrally with the front group lens barrel 55. A spring receiving section 60a opposed to a through-hole 58d of the stopper section 58b and the actuator holding hole 57c of the holding rod 57b is recessed in the front side stopper 60.

The movable lens unit 48 includes a movable lens barrel 65, which is a movable barrel, and a movable lens 66 held by the movable lens barrel 65.

In the present embodiment, the movable lens barrel 65 is disposed in the rear group lens barrel 57, which is the fixed barrel, and capable of advancing and retracting in the direction along the photographing optical axis O. An operation rod 65a projecting in an outer circumferential direction is provided in the movable lens barrel 65. The operation rod 65a is projected to an outer circumference side of the rear group lens barrel 57 via the slit 57a of the rear group lens barrel 57 and opposed to the stopper section 58b (the holding rod 57b) and the front side stopper 60. In the operation rod 65a, a bearing section 65b opposed to the spring receiving section 60a is provided on a surface side opposed to the front side stopper 60. A shaft member 67 projecting into the spring receiving section 60a is held by the bearing section 65b. Further, a return spring 68, one end side of which is held in the spring receiving section 60a, is wound around an outer circumference of the shaft member 67. The operation rod 65a is urged to a proximal end side (the holding rod 57b side) by the return spring 68.

Note that a cover 69 for water-tightly closing the slit 57a is provided on a projecting end side of the holding rod 57b, the stopper section 58b, the front side stopper 60, and the operation rod 65a.

The actuator 49 includes a guide tube 70, a distal end side of which is held by the actuator holding hole 57c of the holding rod 57b. In the guide tube 70, a push rod 71 capable of projecting from and receding to a distal end of the guide tube 70 is provided. A head section 72 functioning as a contact member separably coming into contact with the operation rod 65a is fixedly provided at a distal end of the push rod 71. In this case, in order to prevent catching and the like of the head section 72 and realize a satisfactory projecting and receding motion (advance and retraction) of the push rod 71, the head section 72 is desirably set to length for disposing at least a part of the head section 72 in the through-hole 58d of the stopper section 58b in both states at a projecting time and a receding time of the push rod 71.

A distal end side of a driving wire 73 inserted through the guide tube 70 is coupled to the push rod 71. A shape memory element 74 made of a shape memory alloy is coupled to a proximal end side of the driving wire 73. Further, in the guide tube 70, a push spring 75 for urging the push rod 71 to the front side stopper 60 side with an urging force stronger than an urging force of the return spring 68 is wound around an outer circumference side of the driving wire 73.

For example, the shape memory element 74 is set to be contracted during heating and expanded during cooling and is held in a stretchable state in the guide tube 70. A not-shown heat source such as a Peltier element is juxtaposed to the shape memory element 74. The heat source is capable of heating or cooling the shape memory element 74 according to a state of operation on the operation lever 24. Note that the shape memory element 74 is not limited to a type to be contracted and expanded by heating or cooling using the heat source such as the Peltier element. It is also possible to adopt, for example, a type for heating the shape memory alloy with energization to contract and expand the shape memory alloy.

When the shape memory element 74 is expanded by the cooling, the shape memory element 74 moves the driving wire 73 in a direction for releasing the urging force of the push spring 75 (i.e., a direction of a distal end side along the photographing optical axis O). Consequently, a distal end side of the push rod 71 is projected from the guide tube 70 and presses the operation rod 65a while resisting the urging force of the return spring 68. Consequently, the operation rod 65a moves to a position where the operation rod 65a comes into contact with the front side stopper 60. According to the movement of the operation rod 65a, the movable lens barrel 65 moves the movable lens 66 to an advanced position for realizing a first focal length (a first optical characteristic) set in advance (see FIG. 3).

On the other hand, when the shape memory element 74 is contracted by the heating, the shape memory element 74 moves the driving wire 73 in a direction (i.e., a direction of a proximal end side along the photographing optical axis O) in which the driving wire 73 resists the urging force of the push spring 75. Consequently, the distal end side of the push rod 71 is retracted into the guide tube 70. Consequently, the operation rod 65a is urged by the return spring 68 to move to a position where the operation rod 65a comes into contact with the stopper section 58b. According to the movement of the operation rod 65a, the movable lens barrel 65 moves the movable lens 66 to a retracted position for realizing a second focal length (a second optical characteristic) set in advance (see FIG. 4).

In the image pickup unit 30 configured as explained above, the advanced position of the movable lens 66 for realizing the first focal length is finely adjusted by, for example, adjusting relative positions of respective fixed barrels and the like during assembly of the observation optical system unit 32. That is, when the observation optical system unit 32 is assembled, in a state in which the operation rod 65a is in contact with the front side stopper 60, relative positions of the front group lens barrel 55 and the rear group lens barrel 57 are determined while checking optical characteristics of the front group lens barrel 55 and the rear group lens barrel 57 and fixed via an adhesive or the like.

On the other hand, the retracted position of the movable lens 66 for realizing the second focal length is finely adjusted by, for example, adjusting the position in the photographing optical axis O direction of the stopper member 58 on the rear group lens barrel 57 using the adjustment ring 59 after the front group lens barrel 55 and the rear group lens barrel 57 are positioned and fixed. That is, when the retracted position of the movable lens 66 is adjusted, for example, as shown in FIG. 6, the stopper member 58 and the adjustment ring 59 are fit on the outer circumferential surface of the rear group lens barrel 57 positioned and fixed with respect to the front group lens barrel 55. Thereafter, in a state in which the operation rod 65a is set in contact with the stopper section 58b, the stopper member 58 is positioned by turning the adjustment ring 59 while checking an optical characteristic and fixed via an adhesive or the like.

According to the embodiment explained above, the stopper member 58 is positioned and fixed in a state in which the stopper member 58 is abutted against the outer circumferential surface of the rear group lens barrel 57, movement to a retraction side along the photographing optical axis O of the movable lens barrel 65 is restricted by contact of the stopper section 58b of the stopper member 58 and the operation rod 65a, and the movable lens 66 is held in the position for realizing the second focal length. Consequently, it is possible to prevent axis deviation of the movable lens barrel 65 (the movable lens 66) and obtain a high-quality picked-up image.

That is, the respective fixed barrels such as the rear group lens barrel 57 are basically manufactured with high accuracy. By positioning and fixing an inner circumferential surface of the ring section 58a of the stopper member 58 with respect to the outer circumferential surface of the rear group lens barrel 57 manufactured at high accuracy in this way in a state in which the inner circumferential surface of the ring section 58a is directly abutted against the outer circumferential surface of the rear group lens barrel 57 by surface contact, compared with when the inner circumferential surface of the ring section 58a and the outer circumferential surface of the rear group lens barrel 57 are positioned using a screw section or the like, it is possible to highly accurately fix the stopper section 58b on the rear group lens barrel 57. Therefore, for example, it is possible to highly accurately dispose a contact surface of the stopper section 58b with the operation rod 65a perpendicularly to the photographing optical axis O. Even when the retracted position of the movable lens barrel 65 is specified by the operation rod 65a separated from an axis of the movable lens barrel 65, it is possible to accurately prevent axis deviation from occurring in a tilt direction. In this case, in particular, the stopper section 58b in the present embodiment is formed in a pipe shape and an end face of the stopper section 58b disposed perpendicularly to the photographing optical axis O can be set in contact (in the present embodiment, more specifically, in surface contact) with the operation rod 65a at two or more points. Therefore, it is possible to more suitably prevent axis deviation in the tilt direction of the movable lens barrel 65 (the movable lens 66) with respect to the photographing optical axis O.

The stopper member 58 in the present embodiment is configured by a member formed in a "substantial figure eight shape" in which the ring section 58a having the C-shaped ring shape and the pipe-shaped stopper section 58b are integrally formed. The ring section 58a can be directly abutted over a wide range in a circumferential direction of a circumference of the rear group lens barrel 57. Therefore, it is possible to more highly accurately dispose the contact surface of the stopper section 58b with the operation rod 65a perpendicularly to the photographing optical axis O.

Figure 8:
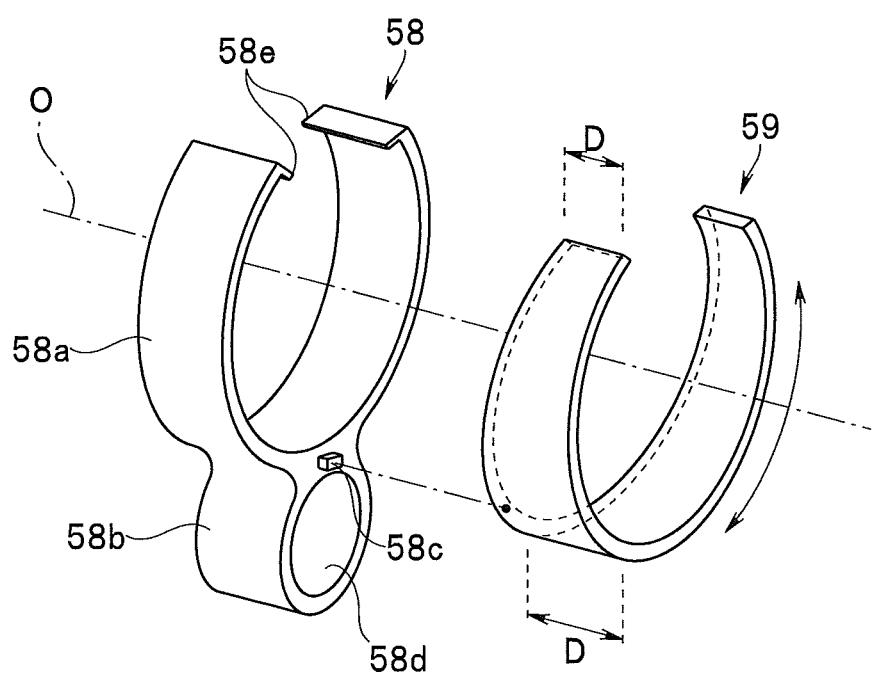
FIG. 8 is a perspective view showing a stopper member and an adjustment ring according to a first modification of the first embodiment of the present invention.
Figure 9:
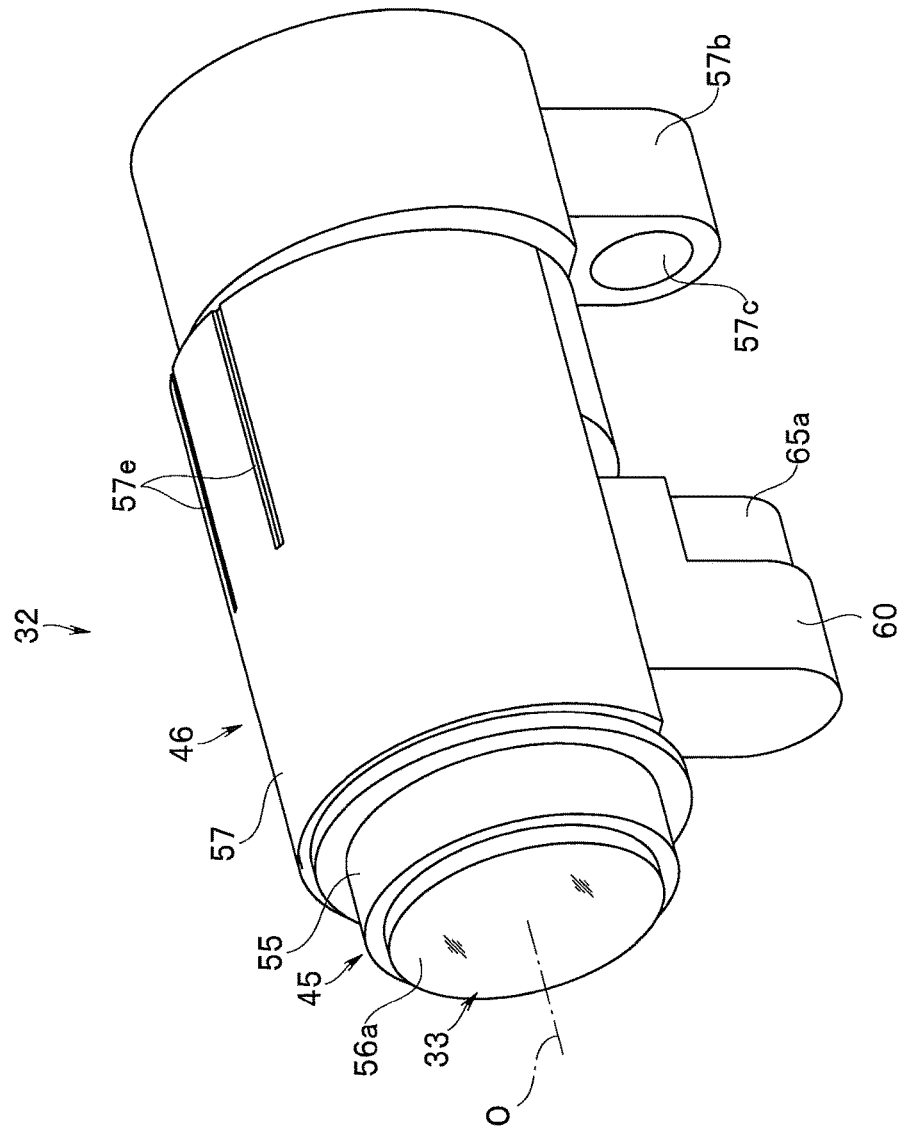
FIG. 9 is a perspective view showing a main part of an observation optical system unit according to the first modification of the first embodiment of the present invention.
Figure 10:
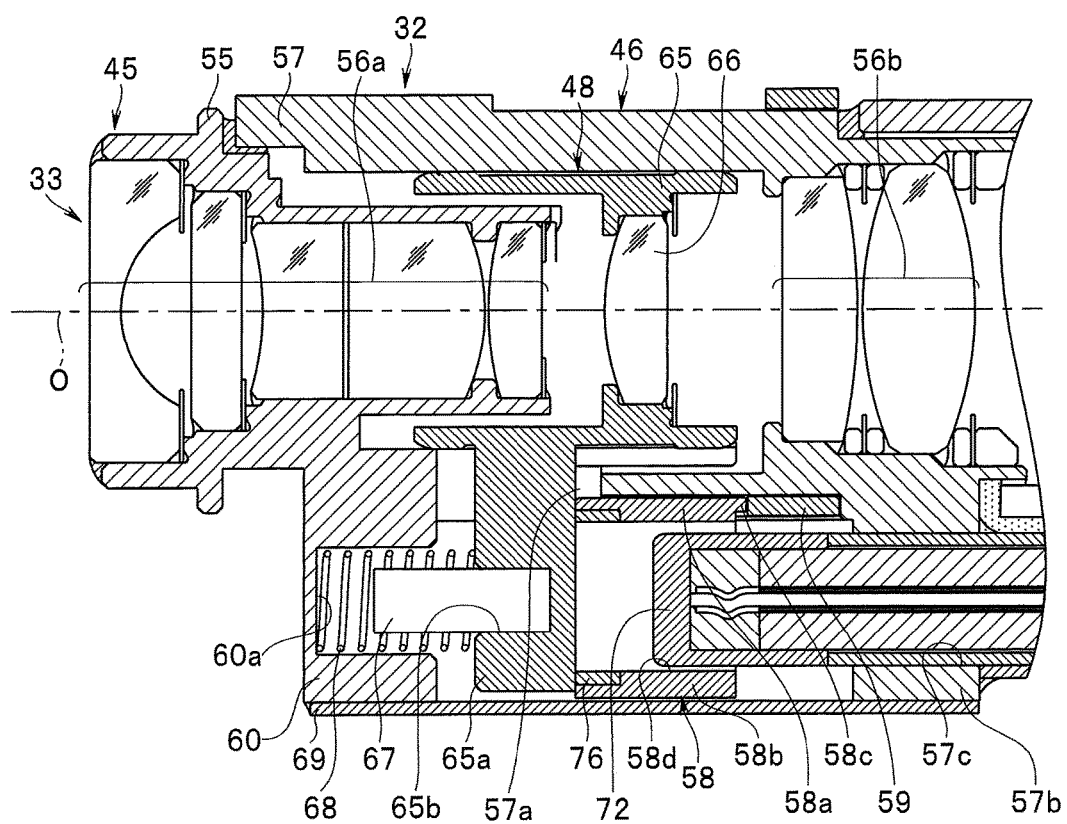
FIG. 10 is a main part sectional view of an observation optical system unit according to a second modification of the first embodiment of the present invention.

In order to improve positioning accuracy of the stopper section 58b around the photographing optical axis O, it is also possible to, for example, provide an inward key 58e at an end portion of the ring section 58a (see FIG. 8), provide a key groove 57e extending in the photographing optical axis O direction on the outer circumferential surface of the rear group lens barrel 57 (see FIG. 9), and fit the key 58e and the key groove 57e during assembly. With such a configuration, it is possible to accurately position the stopper section 58b in a position right opposed to the operation rod 65a and the like.

In order to accurately set the operation rod 65a in contact at the two or more points, it is also possible to dispose a magnet 76 for magnetizing the operation rod 65a on the contact surface side of the stopper member 58.

Figure 11:
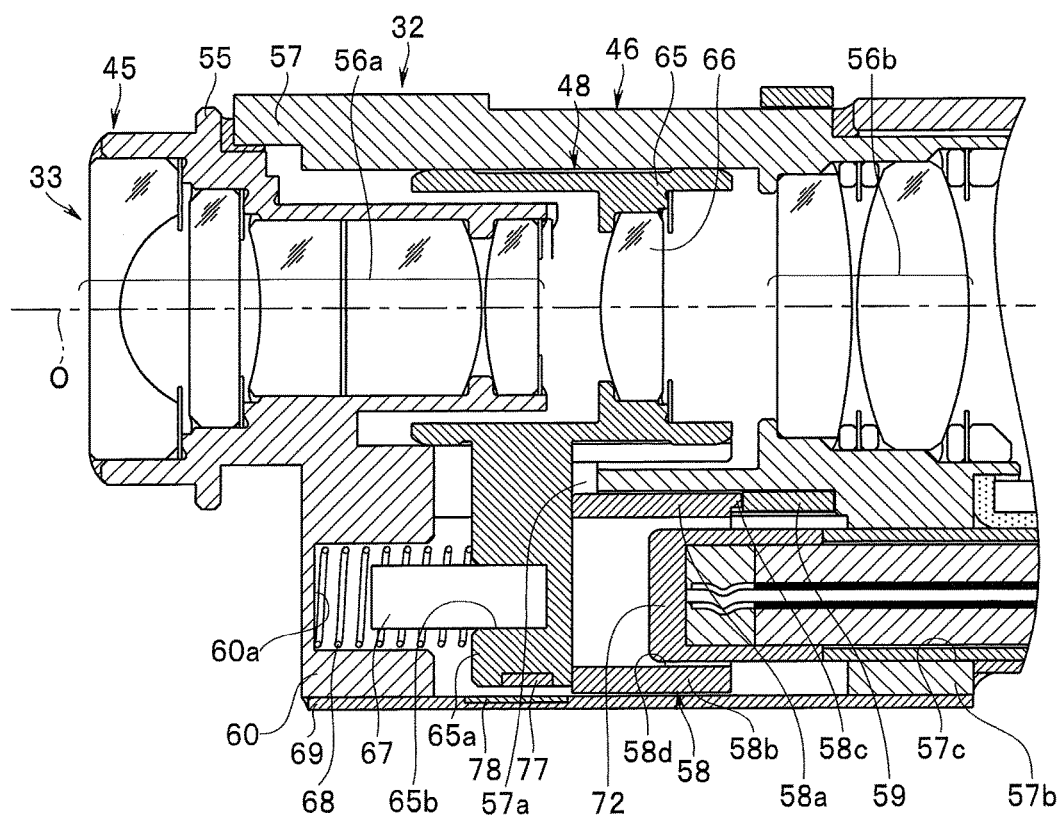
FIG. 11 is a main part sectional view of an observation optical system unit according to a third modification of the first embodiment of the present invention.
Figure 12:
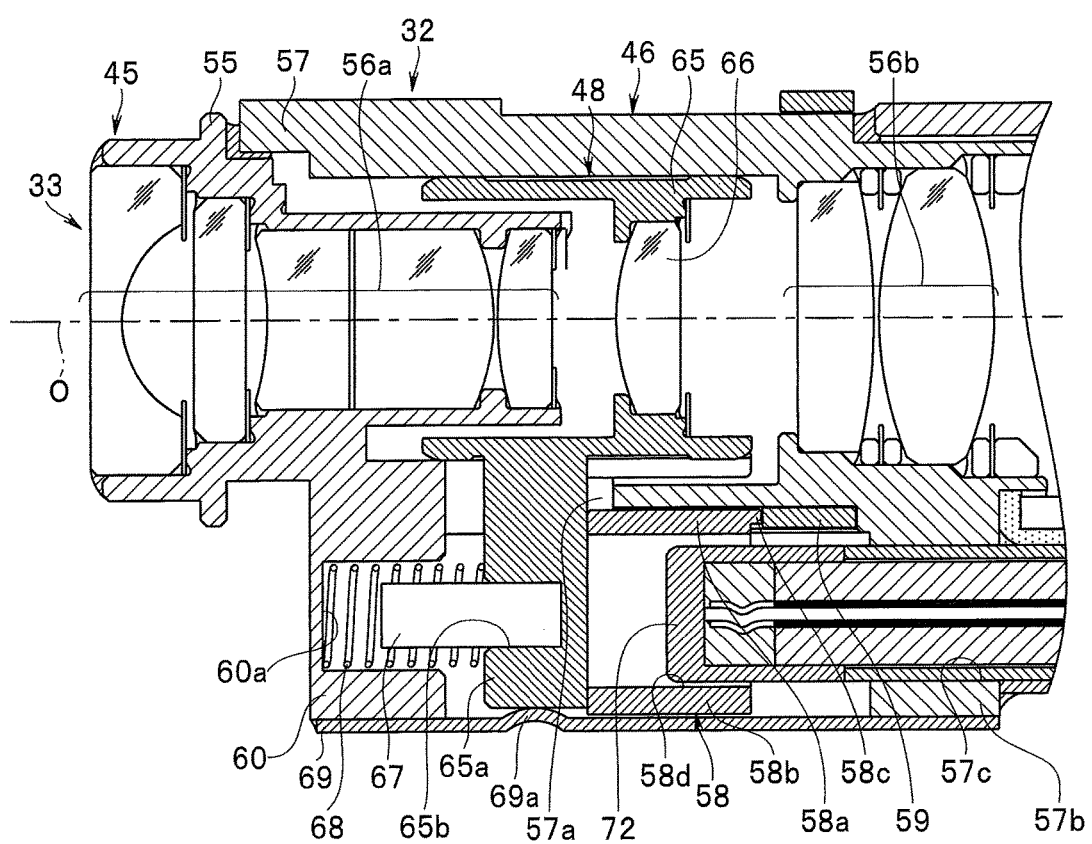
FIG. 12 is a main part sectional view of an observation optical system unit according to a fourth modification of the first embodiment of the present invention.

In order to set the inner circumferential surface of the rear group lens barrel 57 and the outer circumferential surface of the movable lens barrel 65 always in the same direction and prevent the movable lens barrel 65 from being offset in a direction parallel to the photographing optical axis O with respect to a specified position, it is also possible to, for example, as shown in FIG. 11, dispose magnets 77 and 78 opposed to each other in the same polarity (e.g., an S pole and an S pole or an N pole and an N pole) in the operation rod 65a and the cover 69 and urge the movable lens barrel 65 in a direction opposite to a projecting direction of the operation rod 65a. Alternatively, it is also possible to, for example, as shown in FIG. 12, form an inward projecting section for guide 69a in a part of the cover 69 and guide, with the projecting section for guide 69a, the movable lens barrel 65 in the direction opposite to the projecting direction of the operation rod 65a.

Figure 13:
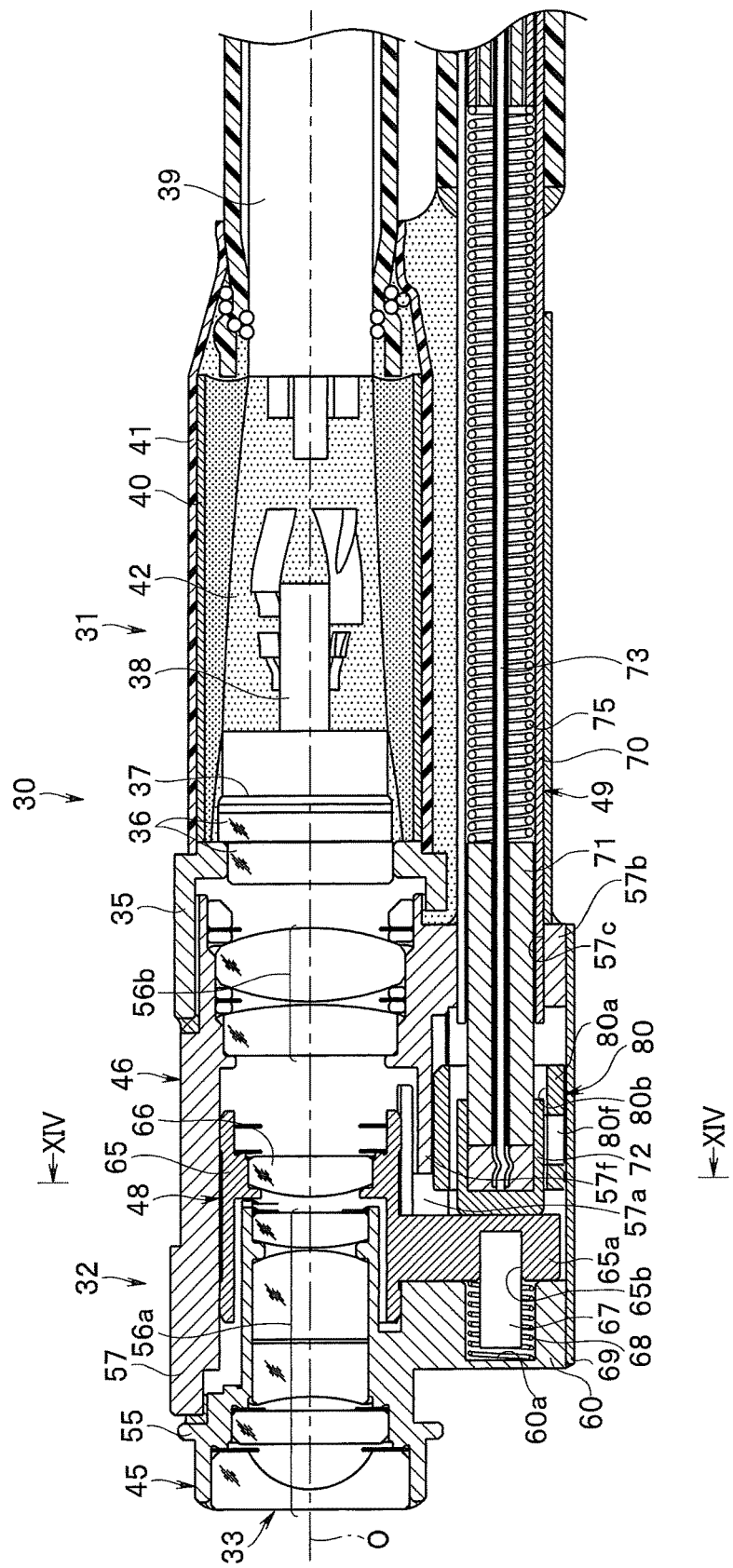
FIG. 13 is a sectional view showing a configuration of an image pickup unit according to a second embodiment of the present invention.
Figure 14:
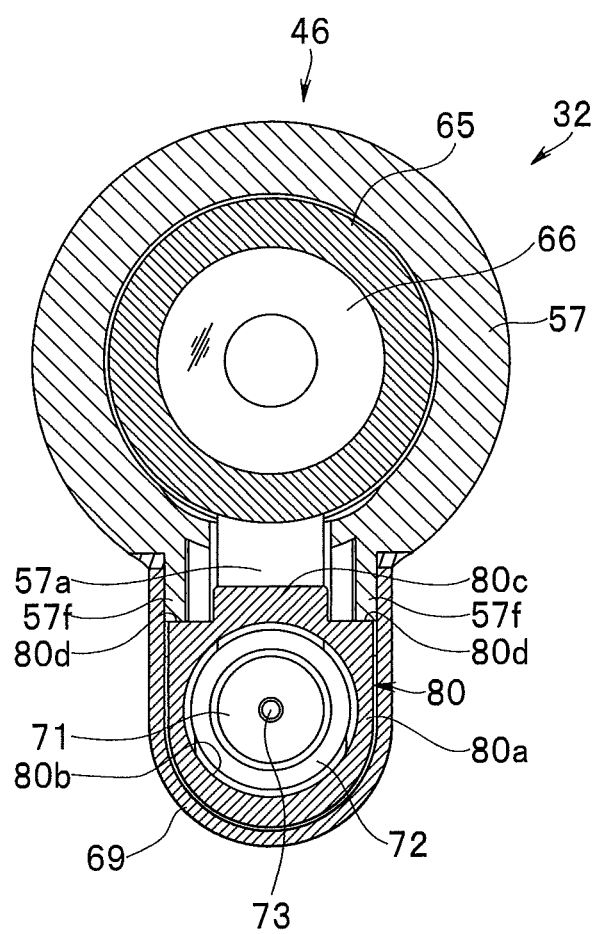
FIG. 14 is a sectional view taken along line XIV-XIV in FIG. 13 according to the second embodiment of the present invention.
Figure 15:
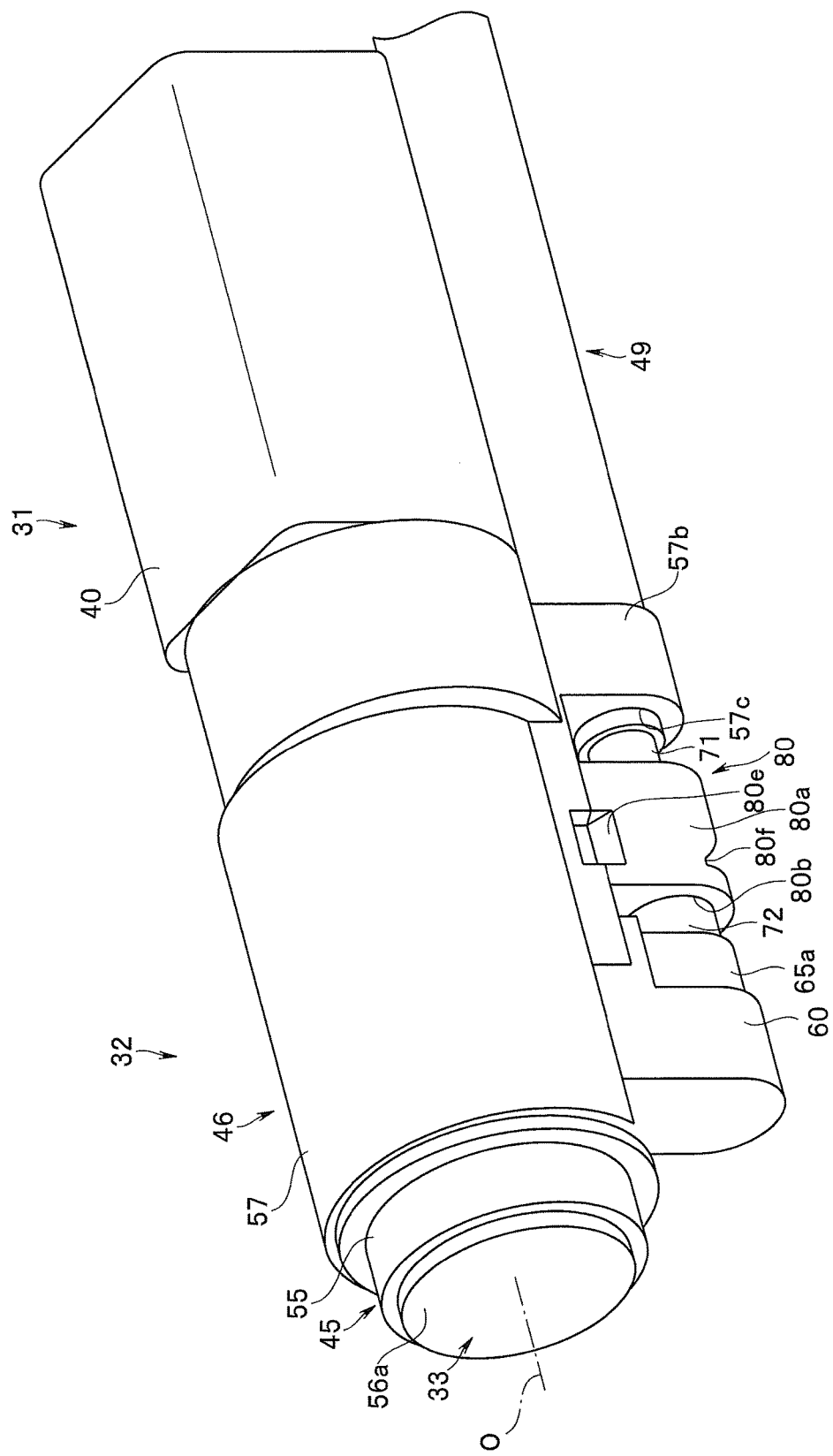
FIG. 15 is a perspective view of the image pickup unit according to the second embodiment of the present invention.
Figure 16:
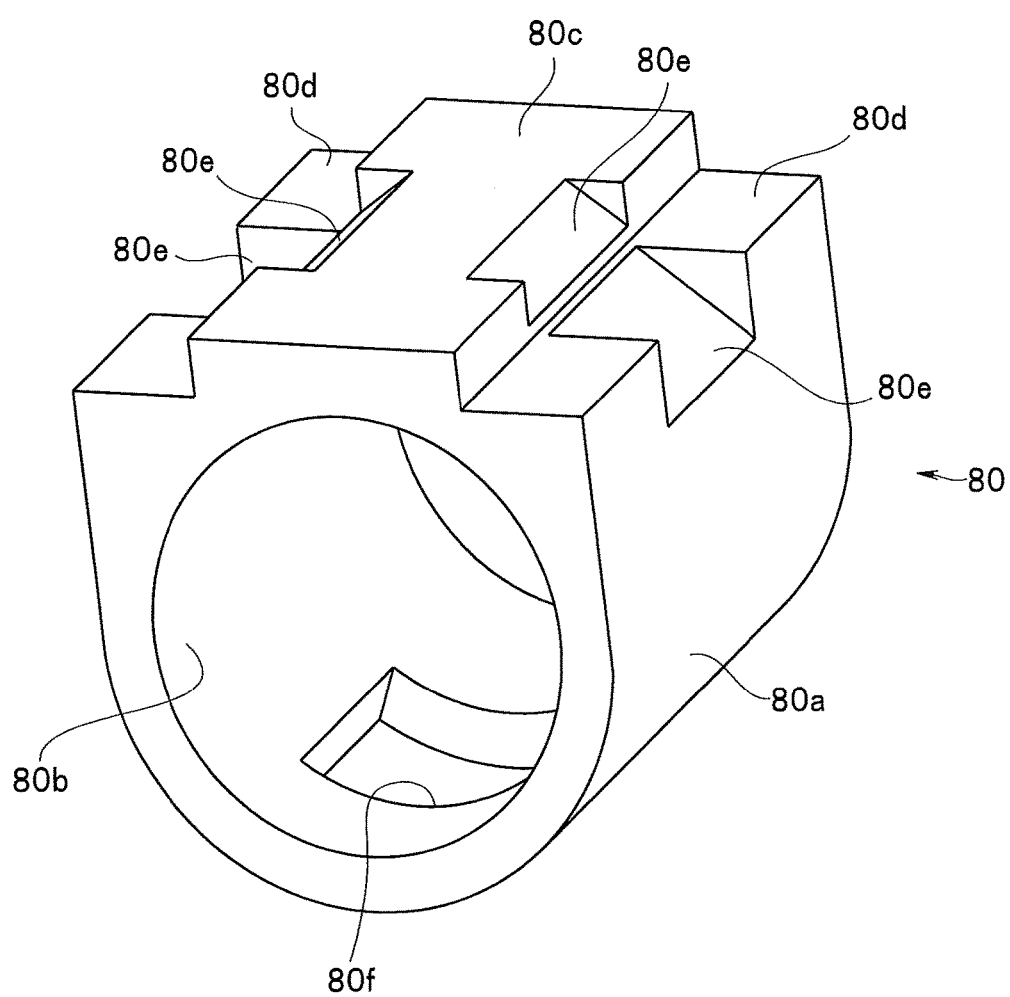
FIG. 16 is a perspective view of a stopper member according to the second embodiment of the present invention.

FIG. 13 to FIG. 16 relate to a second embodiment of the present invention. FIG. 13 is a sectional view showing a configuration of an image pickup unit. FIG. 14 is a sectional view taken along line XIV-XIV in FIG. 13. FIG. 15 is a perspective view of the image pickup unit. FIG. 16 is a perspective view of a stopper member. Note that the present embodiment is mainly different from the first embodiment in a configuration of the stopper member for specifying the retracted position of the movable lens barrel 65. Otherwise, components same as the components in the first embodiment are denoted by the same reference numerals and signs and explanation of the components is omitted.

As shown in FIG. 13 to FIG. 15, in the rear group lens barrel 57, a stopper member 80 positioned and fixed in a state in which the stopper member 80 is abutted against an outer surface of the rear group lens barrel 57 is provided.

More specifically, on a distal end side of the holding rod 57b, a pair of ridge sections 57f is provided in the rear group lens barrel 57. The ridge sections 57f are extended to be parallel to each other along the photographing optical axis O direction on the proximal end side of the slit 57a. Further, projecting end faces of the ridge sections 57f are configured by planes parallel to the photographing optical axis O direction.

As shown in FIG. 16, the stopper member 80 is configured centering on a pipe-shaped stopper section 80a in which a through-hole 80b extending in the photographing optical axis O direction is opened. On one side in a radial direction of the stopper section 80a, a key 80c disposed between the pair of ridge sections 57f formed in the rear group lens barrel 57 is integrally formed. On both sides of the key 80c, adhesive surfaces 80d directly abutted against the projecting end faces of the respective ridge sections 57f by surface contact are formed. Further, in required parts of the key 80c and the adhesive surfaces 80d, cutout sections 80e for reducing sliding resistance of the respective ridge sections 57f and the like and the adhesive surfaces 80d and the like when the stopper member 80 is positioned with respect to the rear group lens barrel 57 and introducing an adhesive between the respective ridge sections 57f and the like and the adhesive surfaces 80d and the like when the stopper member 80 is bonded and fixed to the rear group lens barrel 57 are provided. On the other side in the radial direction of the stopper section 80a, an engaging hole 80f functioning as an engaging section for engaging with a jig (not shown in the figure) when the stopper member 80 is positioned with respect to the rear group lens barrel 57 is provided.

The stopper member 80 is disposed, for example, in a state in which the key 80c is disposed between the ridge sections 57f of the rear group lens barrel 57 positioned and fixed with the front group lens barrel 55 and the adhesive surfaces 80d are abutted against the projecting end faces of the respective ridge sections 57f. Thereafter, in a state in which the operation rod 65a is set in contact with the stopper section 80a, the stopper member 80 is positioned by the jig engaged in the engaging hole 80f while checking an optical characteristic. That is, the stopper member 80 moves while the adhesive surfaces 80d and the like slide with respect to the ridge sections 57f and the like and is positioned with respect to the rear group lens barrel 57. In a state in which the stopper member 80 is positioned in this way, the adhesive is introduced between the stopper member 80 and the ridge sections 57f via the cutout sections 80e, whereby the stopper member 80 is fixed to the rear group lens barrel 57.

According to the embodiment explained above, it is possible to achieve effects same as the effects in the first embodiment explained above. In this case, in the present embodiment, the stopper member 80 is positioned by the jig while being slid with respect to the rear group lens barrel 57. Since the cutout sections 80e are provided in parts of, for example, the adhesive surfaces 80d, which are sliding surfaces in performing the positioning, it is possible to reduce sliding resistance between the rear group lens barrel 57 and the stopper member 80. Therefore, when a position of the stopper member 80 is finely adjusted, it is unnecessary to apply a large force to the stopper member 80. It is possible to accurately position the stopper member 80 without causing, for example, an increase in size of the jig. Since the engaging hole 80f (the engaging section) for engaging with the jig for positioning is provided in the stopper member 80, it is unnecessary to provide, in the stopper member 80, a grasping section or the like to be grasped by the jig. It is possible to prevent an increase in size of the stopper member 80.

Figure 17:
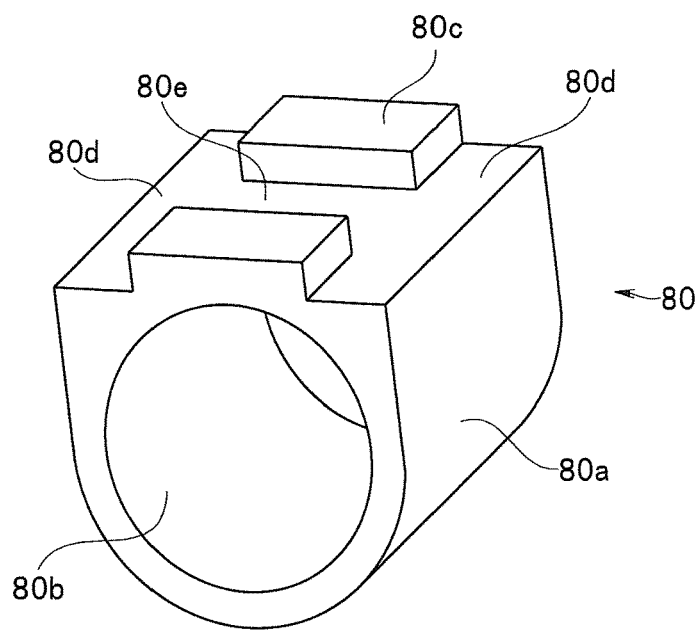
FIG. 17 is a perspective view of a stopper member according to a first modification of the second embodiment of the present invention.
Figure 18:
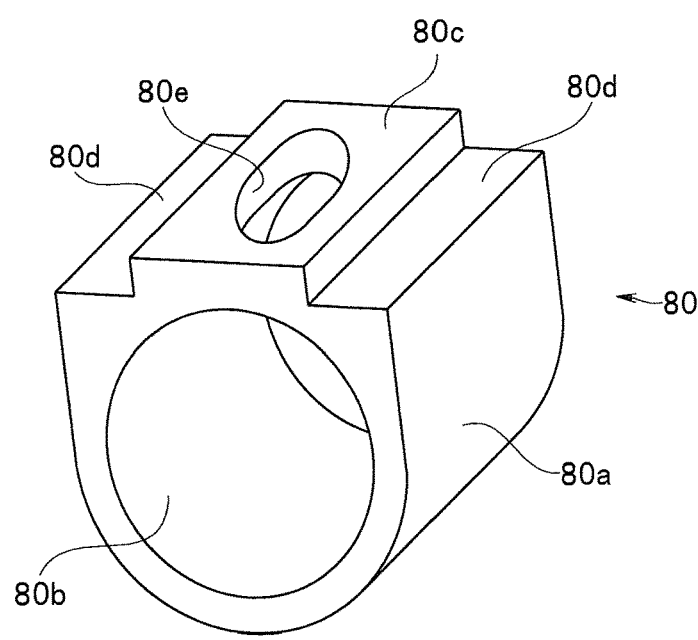
FIG. 18 is a perspective view of a stopper member according to a second modification of the second embodiment of the present invention.

Various modifications are possible concerning the cutout sections provided in the stopper member 80. For example, as shown in FIG. 17, instead of the cutout sections 80e individually provided in the key 80c and the adhesive surfaces 80d, it is also possible to provide the cutout section 80e continuing to both the adhesive surfaces 80d across the key 80c. Alternatively, for example, as shown in FIG. 18, it is also possible to provide the cutout section 80e piercing through from the key 80c to the through-hole 80b of the stopper section 80a.

Figure 19:
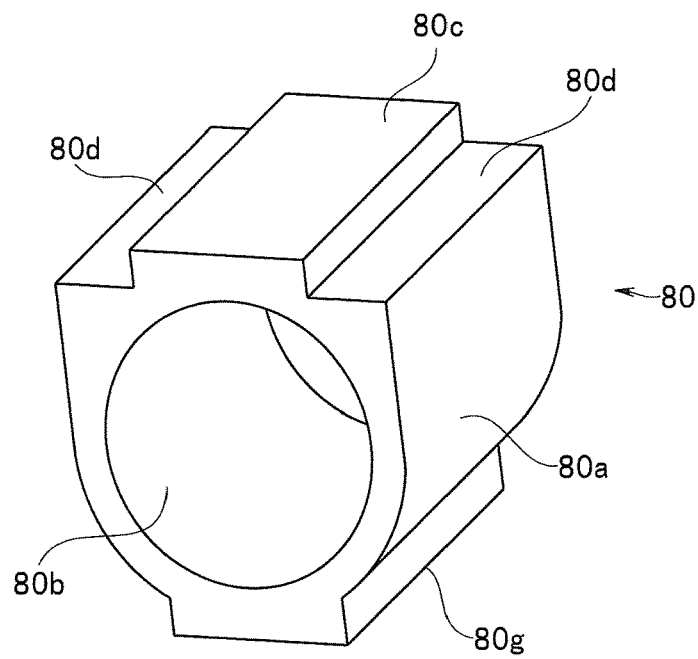
FIG. 19 is a perspective view of a stopper member according to a third modification of the second embodiment of the present invention.
Figure 20:
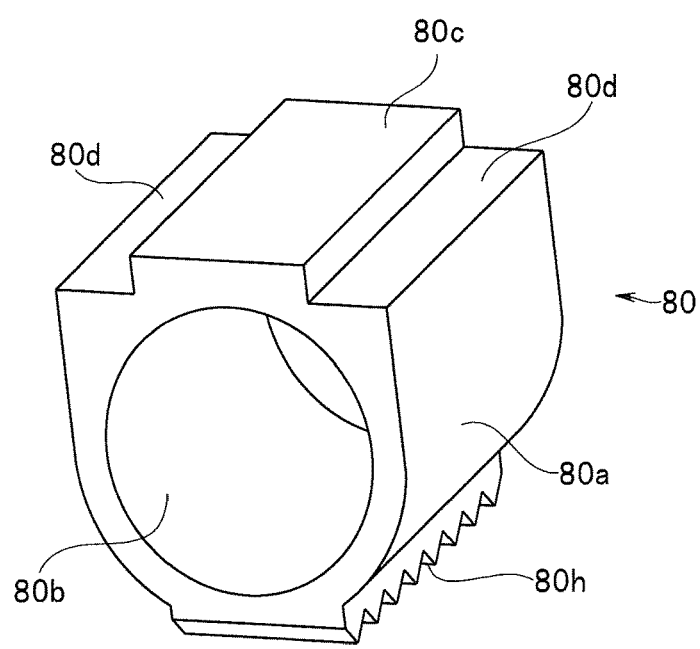
FIG. 20 is a perspective view of a stopper member according to a fourth modification of the second embodiment of the present invention.

Various modifications are also possible concerning a component to be engaged with the jig. For example, as shown in FIG. 19, instead of the engaging hole 80f, it is also possible to provide a protrusion-shaped engaging section 80g. Alternatively, for example, as shown in FIG. 20, instead of the engaging hole 80f, it is also possible to provide a rack gear-shaped engaging section 80h.

Figure 21:
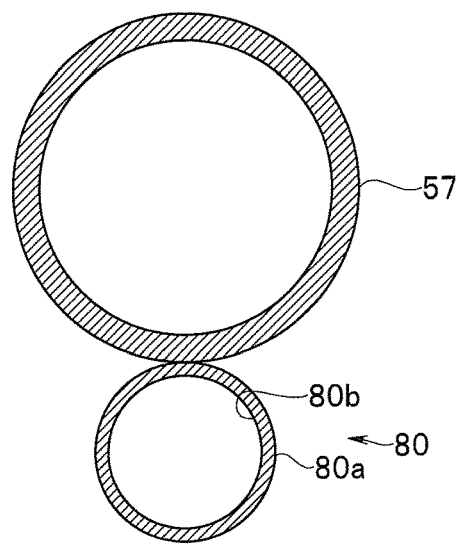
FIG. 21 is a main part sectional view schematically showing a relation between a rear group lens barrel and a stopper member according to a fifth modification of the second embodiment of the present invention.

As a component for positioning and fixing the stopper member 80 in a state in which the stopper member 80 is abutted against the outer circumferential surface of the rear group lens barrel 57 at the two or more points, simpler various modifications are possible. For example, as shown in FIG. 21, it is also possible to fix the stopper member 80 formed in a pipe shape using the adhesive or the like in a state in which the stopper member 80 is abutted against the outer circumferential surface of the rear group lens barrel 57 by line contact.

Figure 22:
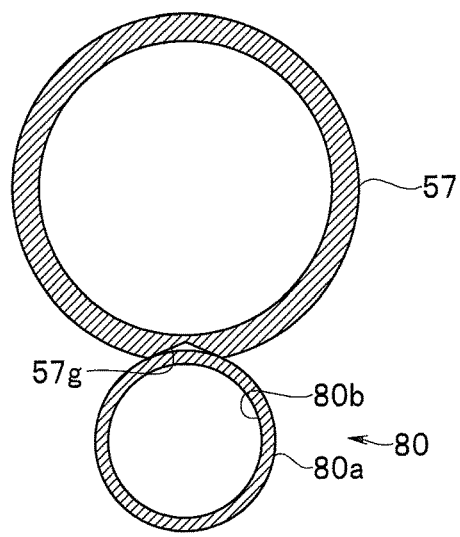
FIG. 22 is a main part sectional view schematically showing a relation between a rear group lens barrel and a stopper member according to a sixth modification of the second embodiment of the present invention.

Alternatively, for example, as shown in FIG. 22, it is also possible to provide a V-shaped cutout section 57g on the outer circumferential surface of the rear group lens barrel 57 and, in a state in which two parts of the stopper member 80 formed in the pipe shape are abutted against the cutout section 57g by line contact, fix the stopper member 80 using the adhesive or the like.

Figure 23:
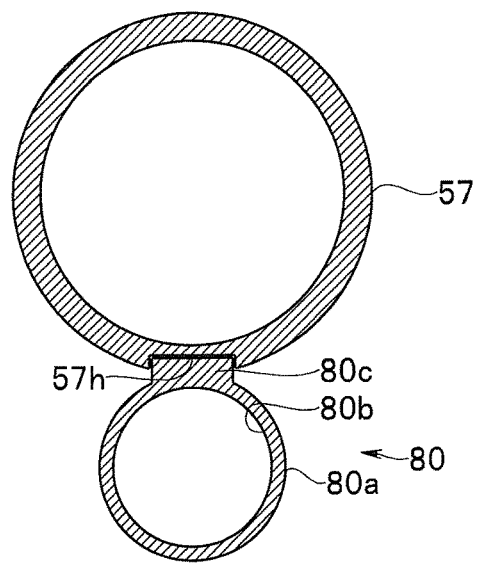
FIG. 23 is a main part sectional view schematically showing a relation between a rear group lens barrel and a stopper member according to a seventh modification of the second embodiment of the present invention.

Alternatively, for example, as shown in FIG. 23, it is also possible to provide a key groove 57h in a part of the outer circumferential surface of the rear group lens barrel 57 and, in a state in which a projecting end face of the key 80c provided in the stopper member 80 is abutted against the key groove 57h by surface contact, fix the stopper member 80 using the adhesive or the like.

Figure 24:
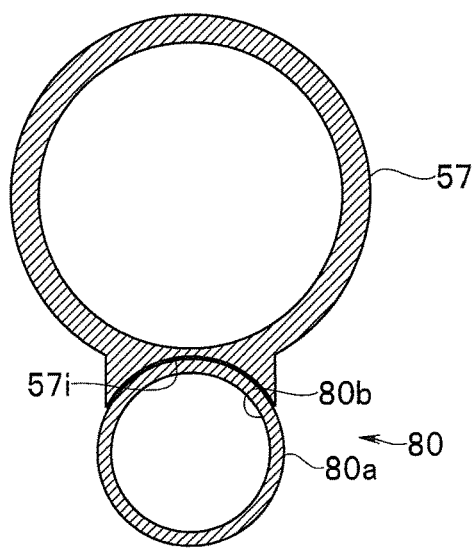
FIG. 24 is a main part sectional view schematically showing a relation between a rear group lens barrel and a stopper member according to an eighth modification of the second embodiment of the present invention.

Alternatively, for example, as shown in FIG. 24, it is also possible to provide a stopper receiving section 57i, a sectional shape of which is formed in a partial arcuate shape, in a part of the outer circumferential surface of the rear group lens barrel 57 and, in a state in which the stopper member 80 formed in the pipe shape is abutted against the stopper receiving section 57i by surface contact, fix the stopper member 80 using the adhesive or the like.

Figure 25:
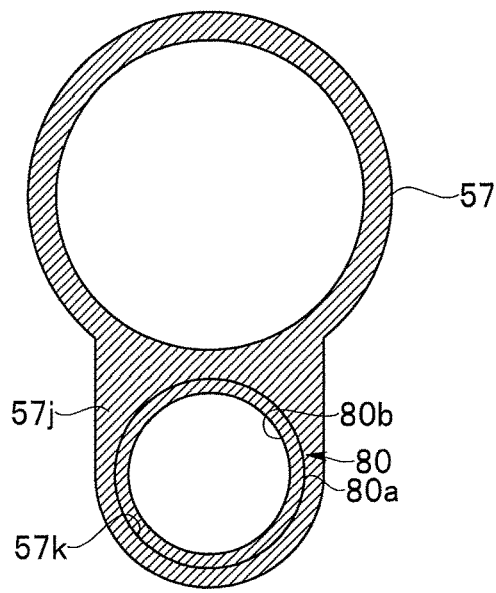
FIG. 25 is a main part sectional view schematically showing a relation between a rear group lens barrel and a stopper member according to a ninth modification of the second embodiment of the present invention.

Alternatively, for example, as shown in FIG. 25, it is also possible to provide a protrusion section 57j including a through-hole 57k in a part of the rear group lens barrel 57 and, in a state in which the outer circumferential surface of the stopper member 80 formed in the pipe shape is abutted against an inner circumferential surface of the through-hole 57k by surface contact, fix the stopper member 80 using the adhesive or the like.

Figure 26:
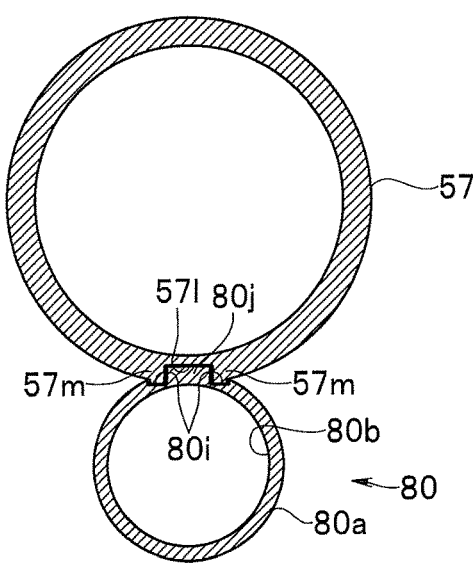
FIG. 26 is a main part sectional view schematically showing a relation between a rear group lens barrel and a stopper member according to a tenth modification of the second embodiment of the present invention.

Alternatively, for example, as shown in FIG. 26, it is also possible to respectively provide, in the rear group lens barrel 57 and the stopper member 80, key grooves 57l and 80i and keys 57m and 80j corresponding to the rear group lens barrel 57 and the stopper member 80 and, in a state in which the key grooves 57l and 80i and the keys 57m and 80j are abutted against each other by surface contact, fix the stopper member 80 using the adhesive or the like.

Figure 27:
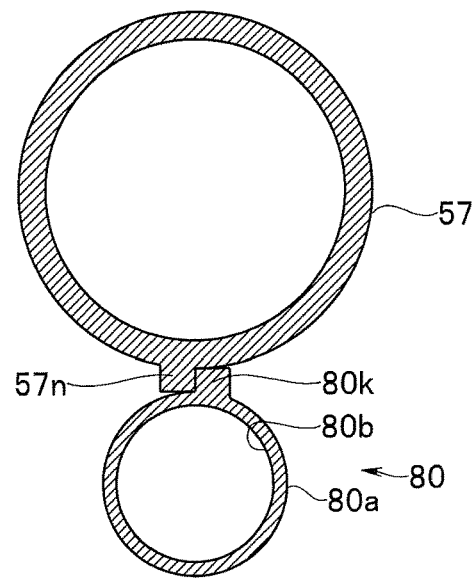
FIG. 27 is a main part sectional view schematically showing a relation between a rear group lens barrel and a stopper member according to an eleventh modification of the second embodiment of the present invention.

Alternatively, for example, as shown in FIG. 27, it is also possible to respectively provide keys 57n and 80k offset from a radial direction in the rear group lens barrel 57 and the stopper member 80 and, in a state in which side surfaces of the keys 57n and 80k are abutted by surface contact, fix the stopper member 80 using the adhesive or the like.

Figure 28:
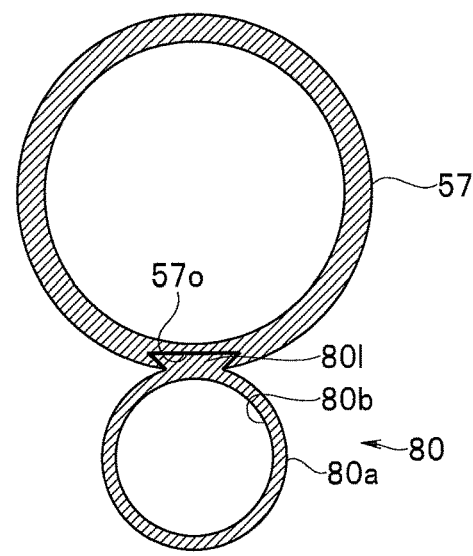
FIG. 28 is a main part sectional view schematically showing a relation between a rear group lens barrel and a stopper member according to a twelfth modification of the second embodiment of the present invention.

Alternatively, for example, as shown in FIG. 28, it is also possible to provide a key groove 57o narrowed toward an outer diameter direction in the rear group lens barrel 57 and provide a key 80l widened toward the outer diameter direction in the stopper member 80 and, in a state in which side surfaces of the key groove 57o and the key 80l are abutted by surface contact, fix the stopper member 80 using the adhesive or the like.

Figure 29:
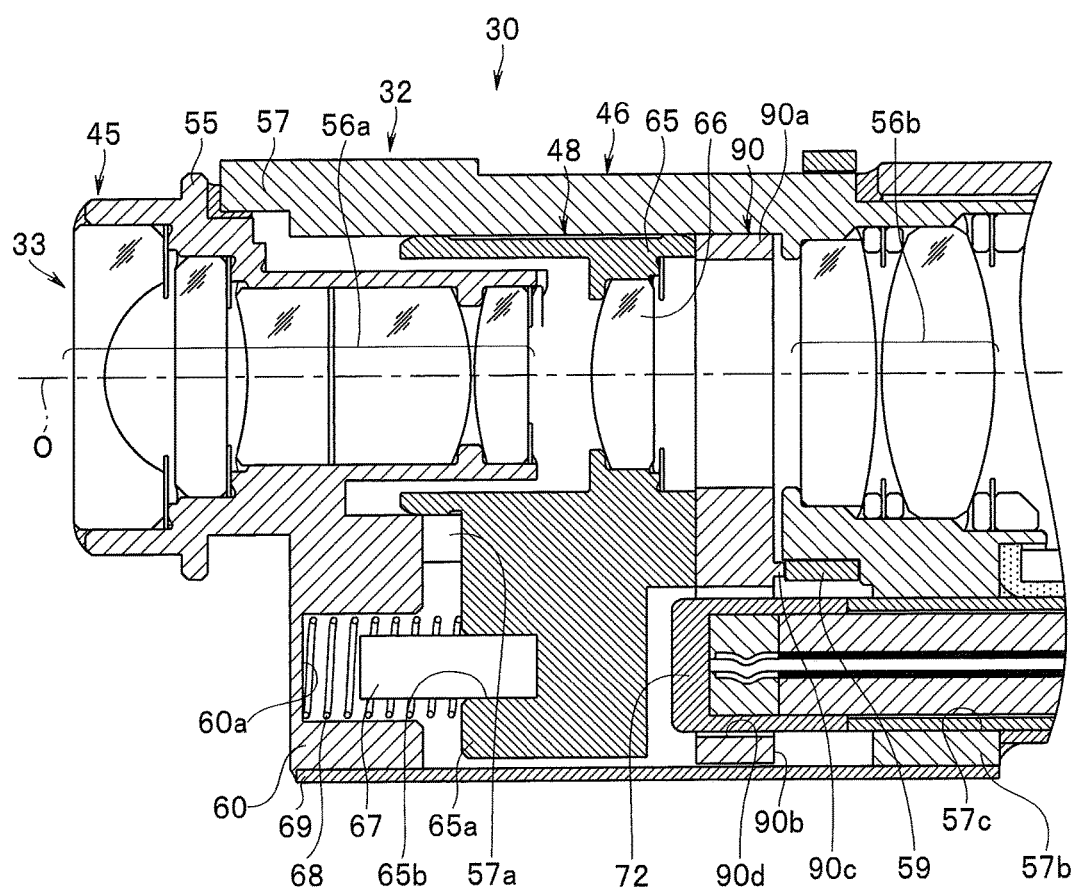
FIG. 29 is a main part sectional view of an observation optical system unit according to a third embodiment of the present invention.
Figure 30:
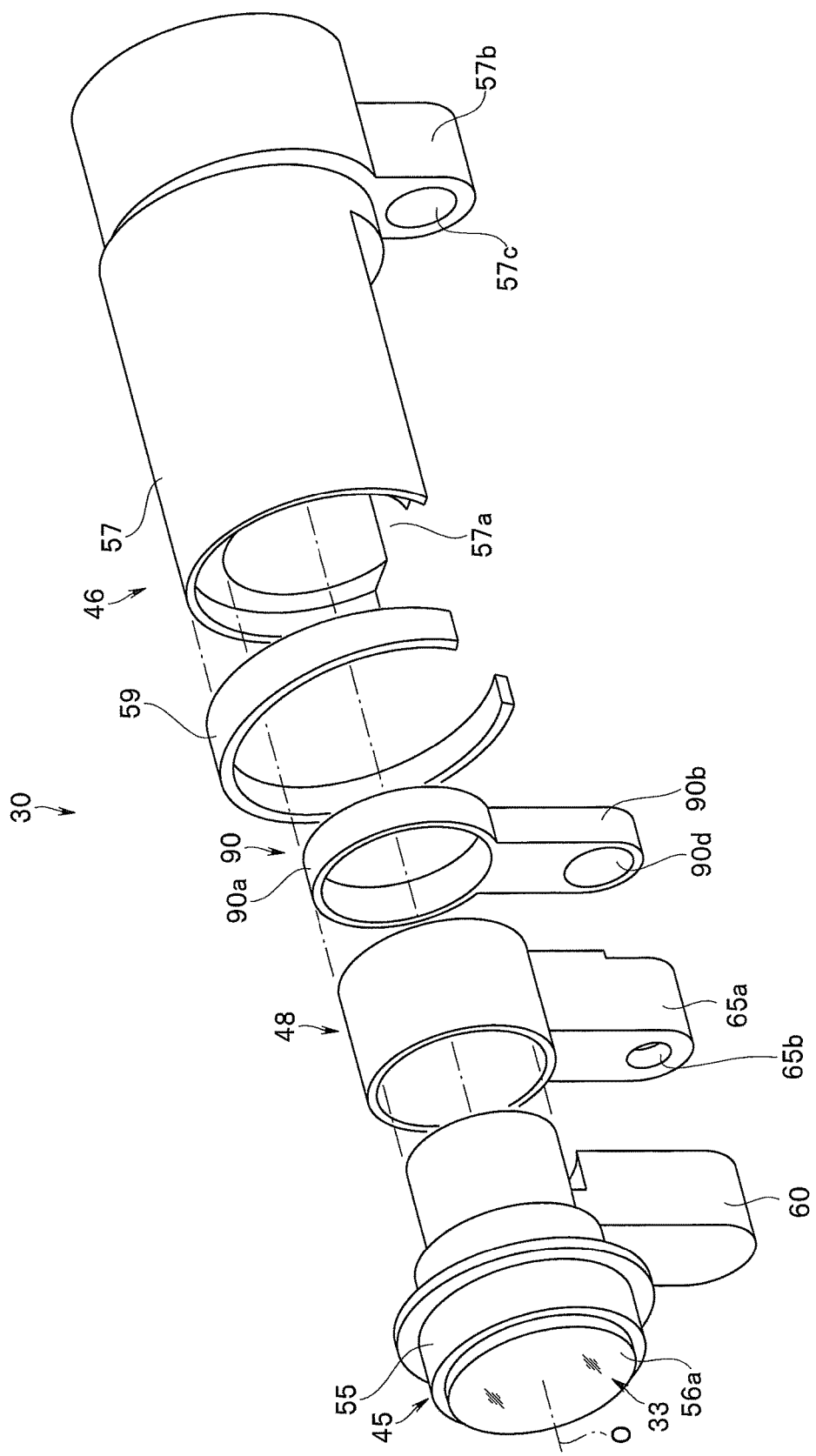
FIG. 30 is an exploded perspective view showing a main part of the observation optical system unit according to the third embodiment of the present invention.

FIGS. 29 and 30 relate to a third embodiment of the present invention. FIG. 29 is a main part sectional view of an observation optical system unit. FIG. 30 is an exploded perspective view showing a main part of the observation optical system unit. Note that the present embodiment is mainly different from the first embodiment in that a stopper member 90 positioned and fixed on the inner circumferential surface of the rear group lens barrel 57 is adopted instead of the stopper member 58 positioned and fixed on the outer circumferential surface of the rear group lens barrel 57. Otherwise, components same as the components in the first embodiment are denoted by the same reference numerals and signs and explanation of the components is omitted.

As shown in FIG. 29, on an inside of the rear group lens barrel 57, the stopper member 90 is disposed further on a proximal end side than the movable lens barrel 65 and further on a distal end side than the rear group lens 56*b*.

The stopper member 90 includes, for example, as shown in FIGS. 29 and 30, a ring section 90*a* abutted against the inner circumferential surface of the rear group lens barrel 57 in a state in which the ring section 90*a* is directly in surface contact with the inner circumferential surface and a stopper section 90*b* formed integrally with the ring section 90*a*.

Like the operation rod 65*a* of the movable lens barrel 65, the stopper section 90*b* is configured by a rod-shaped member projecting to an outside of the rear group lens barrel 57 via the slit 57*a*. The adjustment ring 59 is disposed on a proximal end side of the stopper section 90*b*. The stopper section 90*b* is substantially set in point contact with the adjustment ring 59 on the outside of the rear group lens barrel 57 via a protrusion section 90*c* projecting from the stopper section 90*b*. A through-hole 90*d* opposed to the actuator holding hole 57*c* is provided near a projecting end portion of the stopper section 90*b*.

The stopper member 90 is fixed by bonding the ring section 90*a* to the inner circumferential surface of the rear group lens barrel 57 or/and the slit 57*a* and a root of the stopper 90*b* in a state in which the stopper section 90*b* is positioned to be opposed to the holding rod 57*b* in a predetermined position in the photographing optical axis O direction.

In the image pickup unit 30 configured as explained above, the retracted position of the movable lens 66 for realizing the second focal length is finely adjusted by, for example, after the front group lens barrel 55 and the rear group lens barrel 57 are positioned and fixed, adjusting a position in the photographing optical axis O direction of the stopper member 90 in the rear group lens barrel 57 using the adjustment ring 59. That is, in a state in which an end face of the movable lens barrel 65 is set in contact with the ring section 90*a* and the operation rod 65*a* projecting from the movable lens barrel 65 is set in contact with the stopper section 90*b*, the stopper member 90 is positioned by turning the adjustment ring 59 while checking an optical characteristic and fixed via the adhesive or the like.

According to the embodiment explained above, it is possible to achieve effects substantially the same as the effects in the first embodiment. In this case, since the ring section 90*a* of the stopper member 90 is disposed on the inner circumferential surface side of the rear group lens barrel 57, as shown in FIG. 29, in the retracted position of the movable lens barrel 65, it is possible to set the movable lens barrel 65 in contact with (more specifically, set a rear end face of the movable lens barrel 65 in surface contact with) not only the stopper section 90*b* but also the ring section 90*a*. It is possible to more highly accurately realize the positioning of the movable lens barrel 65. Note that, in this embodiment in which a contact area of the movable lens unit 48 and the stopper member 90 can be sufficiently secured by the contact (the surface contact) of the ring section 90*a* with the movable lens barrel 65, it is possible to reduce length of the stopper section 90*b* as appropriate, in particular, in a range in which abutment of the stopper member 90 and the adjustment ring 59 can be realized. Further, it is possible to omit the through-hole 90*d* as appropriate.

Note that the present invention is not limited to the respective embodiments and the respective modifications explained above. Various modifications and changes are possible. The modifications and the changes are also within the technical scope of the present invention. For example, it goes without saying that the configurations of the respective embodiments and the respective modifications may be combined as appropriate.

In the respective embodiments, the example is explained in which the image pickup unit is applied to the endoscope. However, the present invention is not limited to this. It goes without saying that the image pickup unit can also be applied to other electronic apparatuses.

What is claimed is:

1. An image pickup unit comprising:
   an observation optical system of a focus switching type including a fixed lens and a movable lens;
   a fixed barrel that holds the fixed lens;
   a movable barrel disposed in the fixed barrel to be capable of advancing and retracting in a direction along a photographing optical axis of the observation optical system, the movable barrel holding the movable lens;
   a front side stopper that is in contact with the movable barrel at two or more points arranged so as to be vertically separate from each other with respect to the photographing optical axis, the front side stopper restricting movement of the movable barrel in an advancing direction along the photographing optical axis, to hold the movable lens in a position for realizing a first focal length of the observation optical system; and
   a stopper member positioned and fixed in a state in which the stopper member is abutted against an outer surface of the fixed barrel by surface contact, the stopper member having a pipe shape and the pipe shape having an interior cavity and being in contact with the movable barrel at opposite sides of the pipe shape, the opposite sides being vertically separate from each other with respect to a central axis of the pipe shape, the stopper member restricting movement of the movable barrel in a retracting direction along the photographing optical axis, to thereby hold the movable lens in a position for realizing a second focal length of the observation optical system.

2. The image pickup unit according to claim 1, wherein the stopper member is in surface contact with the movable barrel.

3. The image pickup unit according to claim 1, wherein the stopper member includes a ring section positioned and fixed in a state in which the ring section is abutted against an outer circumferential surface of the fixed barrel and a stopper section formed integrally with the ring section and capable of coming into contact with the movable barrel.

4. The image pickup unit according to claim 3, further comprising an end-face-cam adjustment member capable of changing an abutting position against the stopper member by turning around the photographing optical axis to thereby adjust a position in the photographing optical axis direction of the stopper member with respect to the fixed barrel, wherein
   the stopper member is fixed to an outer circumferential surface of the fixed barrel in a state in which the position of the stopper member is adjusted in the photographing optical axis direction by the end-face-cam adjustment member.

5. The image pickup unit according to claim 4, wherein the stopper member includes a protrusion section abutted against the end-face-cam adjustment member.

6. The image pickup unit according to claim 1, wherein the stopper member includes a cutout section in a part of an adhesive surface for positioning with the fixed barrel.

7. The image pickup unit according to claim 1, wherein the stopper member includes an engaging hole capable of engaging with a jig for positioning the stopper member on the fixed barrel.

8. An endoscope comprising the image pickup unit according to claim 1 provided at a distal end portion of an insertion section inserted into a subject.

9. The image pickup unit according to claim 1, wherein the stopper member includes a protrusion configured to engage with a jig for positioning the stopper member on the fixed barrel.

10. The image pickup unit according to claim 1, wherein the stopper member includes a rack gear configured to engage with a jig for positioning the stopper member in the fixed barrel.

* * * * *